United States Patent
Cabiri et al.

(10) Patent No.: US 12,005,237 B2
(45) Date of Patent: Jun. 11, 2024

(54) MEDICAMENT DELIVERY DEVICE COMPRISING A VISUAL INDICATOR

(71) Applicant: West Pharma. Services IL, Ltd., Ra'anana (IL)

(72) Inventors: Oz Cabiri, Macabim-Reut (IL); Ran Hezkiahu, Herzliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 166 days.

(21) Appl. No.: 17/520,655

(22) Filed: Nov. 6, 2021

(65) Prior Publication Data

US 2022/0054754 A1   Feb. 24, 2022

Related U.S. Application Data

(60) Division of application No. 16/071,509, filed as application No. PCT/US2016/056258 on Oct. 10, (Continued)

(51) Int. Cl.
*A61M 5/28*       (2006.01)
*A61M 5/31*       (2006.01)
(Continued)

(52) U.S. Cl.
CPC ............ *A61M 5/28* (2013.01); *A61M 5/3134* (2013.01); *A61M 5/3202* (2013.01); *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/14248* (2013.01); *A61M 5/1456* (2013.01); *A61M 2005/1581* (2013.01); *A61M 2005/312* (2013.01); *A61M 2005/341* (2013.01);
(Continued)

(58) Field of Classification Search
CPC ...... A61M 5/28; A61M 5/3134; A61M 5/315; A61M 5/34; A61M 5/14248; A61M 5/1456; A61M 5/14566
See application file for complete search history.

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1071846 | 5/1993 |
| CN | 1118273 | 3/1996 |

(Continued)

OTHER PUBLICATIONS

US 8,333,733 B2, 12/2012, Lanigan et al. (withdrawn)
(Continued)

*Primary Examiner* — Tasnim Mehjabin Ahmed
(74) *Attorney, Agent, or Firm* — Blank Rome LLP

(57) ABSTRACT

A pharmaceutical delivery device includes a cartridge containing a fluid. The cartridge includes a light pipe section having an input location and a light diffusing section optically coupled to the light pipe. A light source is optically coupled to the cartridge at the input location to the light pipe, such that at least some light from the light source entering at the input location is diffused at the light diffusing section.

11 Claims, 12 Drawing Sheets

Related U.S. Application Data 2016, now Pat. No. 11,311,674, which is a continuation of application No. 15/269,248, filed on Sep. 19, 2016, now Pat. No. 10,086,145, and a continuation of application No. 15/204,542, filed on Jul. 7, 2016, now Pat. No. 10,576,207.

(60) Provisional application No. 62/281,536, filed on Jan. 21, 2016.

(51) Int. Cl.
| | |
|---|---|
| *A61M 5/32* | (2006.01) |
| *A61M 5/34* | (2006.01) |
| *B65D 1/36* | (2006.01) |
| *B65D 5/50* | (2006.01) |
| *B65D 21/02* | (2006.01) |
| *B65D 25/10* | (2006.01) |
| *A61M 5/142* | (2006.01) |
| *A61M 5/145* | (2006.01) |
| *A61M 5/158* | (2006.01) |

(52) U.S. Cl.
CPC . *A61M 2205/3306* (2013.01); *A61M 2207/00* (2013.01)

(56) References Cited

U.S. PATENT DOCUMENTS

| | | |
|---|---|---|
| 1,321,550 A | 11/1919 | Frank et al. |
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A | 12/1987 | Henri et al. |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| D369,864 S | 5/1996 | Petersen |
| D370,011 S | 5/1996 | Lindeman |
| 5,562,624 A | 10/1996 | Righi et al. |
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |
| 5,624,400 A | 4/1997 | Firth et al. |
| 5,637,095 A | 6/1997 | Nason et al. |

(56) References Cited

U.S. PATENT DOCUMENTS

| | | |
|---|---|---|
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Oesterlind et al. |
| 5,690,618 A | 11/1997 | Smith et al. |
| 5,697,908 A | 12/1997 | Imbert et al. |
| 5,697,916 A | 12/1997 | Schraga |
| D389,139 S | 1/1998 | Oross |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,296 A | 12/1999 | Jansen et al. |
| 6,004,297 A | 12/1999 | Steenfeldt-Jensen et al. |
| D421,902 S | 3/2000 | Hill |
| 6,033,245 A | 3/2000 | Yamkovoy |
| 6,033,377 A | 3/2000 | Rasmussen et al. |
| 6,045,533 A | 4/2000 | Kriesel et al. |
| D424,626 S | 5/2000 | Goto |
| 6,064,797 A | 5/2000 | Crittendon et al. |
| 6,074,369 A | 6/2000 | Sage et al. |
| 6,079,979 A | 6/2000 | Riitano |
| 6,162,197 A | 12/2000 | Mohammad |
| 6,186,979 B1 | 2/2001 | Dysarz |
| 6,186,982 B1 | 2/2001 | Gross et al. |
| 6,189,292 B1 | 2/2001 | Odell et al. |
| 6,200,289 B1 | 3/2001 | Hochman et al. |
| 6,200,296 B1 | 3/2001 | Dibiasi et al. |
| D441,185 S | 5/2001 | Shimizu |
| 6,224,569 B1 | 5/2001 | Brimhall |
| D443,508 S | 6/2001 | Braaten |
| 6,248,093 B1 | 6/2001 | Moberg |
| D445,496 S | 7/2001 | Anderson |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,362,591 B1 | 3/2002 | Moberg |
| 6,377,848 B1 | 4/2002 | Garde et al. |
| 6,391,005 B1 | 5/2002 | Lum et al. |
| D460,551 S | 7/2002 | Swenson |
| 6,423,029 B1 | 7/2002 | Elsberry |
| D461,243 S | 8/2002 | Niedospial |
| D461,244 S | 8/2002 | Niermann |
| D461,245 S | 8/2002 | Niermann |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,530,900 B1 | 3/2003 | Daily |
| 6,554,800 B1 | 4/2003 | Nezhadian et al. |
| 6,555,986 B2 | 4/2003 | Moberg |
| D474,543 S | 5/2003 | Lee |
| 6,558,351 B1 | 5/2003 | Steil et al. |
| 6,565,541 B2 | 5/2003 | Sharp |
| 6,585,695 B1 | 7/2003 | Adair et al. |
| 6,589,229 B1 | 7/2003 | Connelly et al. |
| 6,595,956 B1 | 7/2003 | Gross et al. |
| 6,595,960 B2 | 7/2003 | West et al. |
| 6,613,015 B2 | 9/2003 | Sandstrom |
| 6,645,181 B1 | 11/2003 | Lavi et al. |
| 6,652,482 B2 | 11/2003 | Hochman |
| D483,281 S | 12/2003 | Cobigo |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,685,678 B2 | 2/2004 | Evans et al. |
| 6,689,118 B2 | 2/2004 | Alchas et al. |
| 6,699,218 B2 | 3/2004 | Flaherty et al. |
| 6,719,141 B2 | 4/2004 | Heinz et al. |
| 6,722,916 B2 | 4/2004 | Buccinna et al. |
| D490,069 S | 5/2004 | Lee |
| 6,743,211 B1 | 6/2004 | Prausnitz et al. |
| 6,749,587 B2 | 6/2004 | Flaherty |
| 6,752,783 B2 | 6/2004 | Hung et al. |
| 6,752,787 B1 | 6/2004 | Causey et al. |
| 6,767,336 B1 | 7/2004 | Kaplan |
| 6,768,425 B2 | 7/2004 | Flaherty et al. |
| D495,303 S | 8/2004 | Coullahan |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,817,990 B2 | 11/2004 | Yap et al. |
| 6,824,529 B2 | 11/2004 | Gross et al. |
| 6,843,782 B2 | 1/2005 | Gross et al. |
| 6,854,620 B2 | 2/2005 | Ramey |
| 6,889,690 B2 | 5/2005 | Crowder |
| 6,905,298 B1 | 6/2005 | Haring |
| 6,907,679 B2 | 6/2005 | Yarborough et al. |
| 6,908,452 B2 | 6/2005 | Diaz et al. |
| 6,960,192 B1 | 11/2005 | Flaherty et al. |
| 6,979,316 B1 | 12/2005 | Rubin et al. |
| D514,097 S | 1/2006 | De Leon |
| 6,997,727 B1 | 2/2006 | Legrady et al. |
| 7,001,360 B2 | 2/2006 | Veasey et al. |
| 7,004,104 B1 | 2/2006 | Kundus |
| 7,004,929 B2 | 2/2006 | McWethy et al. |
| 7,025,226 B2 | 4/2006 | Ramey |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,063,684 B2 | 6/2006 | Moberg |
| 7,066,909 B1 | 6/2006 | Peter et al. |
| 7,094,221 B2 | 8/2006 | Veasey et al. |
| 7,097,637 B2 | 8/2006 | Triplett et al. |
| 7,112,187 B2 | 9/2006 | Karlsson |
| 7,128,727 B2 | 10/2006 | Flaherty et al. |
| 7,129,389 B1 | 10/2006 | Watson |

(56) References Cited

U.S. PATENT DOCUMENTS

| | | |
|---|---|---|
| 7,144,384 B2 | 12/2006 | Gorman et al. |
| 7,193,521 B2 | 3/2007 | Moberg et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| D552,184 S | 10/2007 | Hussaini |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,306,578 B2 | 12/2007 | Gray et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |
| 7,390,314 B2 | 6/2008 | Stutz et al. |
| 7,407,493 B2 | 8/2008 | Cane |
| 7,418,880 B1 | 9/2008 | Smith |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| RE40,755 E | 6/2009 | McWethy |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| 7,597,682 B2 | 10/2009 | Moberg |
| D604,835 S | 11/2009 | Conley |
| D604,839 S | 11/2009 | Crawford |
| 7,611,491 B2 | 11/2009 | Pickhard |
| 7,621,893 B2 | 11/2009 | Moberg et al. |
| D605,287 S | 12/2009 | Crawford |
| 7,628,770 B2 | 12/2009 | Ethelfeld |
| 7,628,772 B2 | 12/2009 | Mcconnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,658,734 B2 | 2/2010 | Adair et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| D619,338 S | 7/2010 | Teichert |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| D622,685 S | 8/2010 | Garra |
| 7,766,867 B2 | 8/2010 | Lynch et al. |
| 7,766,873 B2 | 8/2010 | Moberg et al. |
| 7,776,030 B2 | 8/2010 | Estes et al. |
| 7,780,636 B2 | 8/2010 | Radmer |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,850,658 B2 | 12/2010 | Faust |
| 7,854,723 B2 | 12/2010 | Wang et al. |
| 7,857,131 B2 | 12/2010 | Vedrine |
| 7,879,025 B2 | 2/2011 | Jacobson et al. |
| 7,892,206 B2 | 2/2011 | Moberg et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,931,621 B2 | 4/2011 | Cross |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| D640,920 S | 7/2011 | Giraud |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 7,998,131 B2 | 8/2011 | Adair et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| D646,159 S | 10/2011 | Bellamah |
| 8,029,469 B2 | 10/2011 | Ethelfeld |
| 8,034,019 B2 | 10/2011 | Nair et al. |
| 8,034,026 B2 | 10/2011 | Grant et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| D651,308 S | 12/2011 | Crawford |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| 8,128,596 B2 | 3/2012 | Carter |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |

(56) References Cited

U.S. PATENT DOCUMENTS

| | | |
|---|---|---|
| 8,162,923 B2 | 4/2012 | Adams et al. |
| D660,420 S | 5/2012 | Shaw |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,210,172 B2 | 7/2012 | Crowder |
| 8,221,356 B2 | 7/2012 | Enggaard et al. |
| D667,382 S | 9/2012 | Cosentino |
| D667,950 S | 9/2012 | Hyun |
| 8,257,345 B2 | 9/2012 | Adair et al. |
| 8,267,893 B2 | 9/2012 | Moberg et al. |
| 8,267,921 B2 | 9/2012 | Yodfat et al. |
| 8,273,061 B2 | 9/2012 | McConnell et al. |
| 8,287,520 B2 | 10/2012 | Drew et al. |
| 8,292,647 B1 | 10/2012 | Mcgrath et al. |
| 8,303,549 B2 | 11/2012 | Mejlhede |
| 8,303,572 B2 | 11/2012 | Adair et al. |
| 8,308,679 B2 | 11/2012 | Hanson et al. |
| 8,308,695 B2 | 11/2012 | Laiosa |
| 8,313,467 B2 | 11/2012 | Chong |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Indegger et al. |
| 8,393,357 B2 | 3/2013 | Chong |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| D683,848 S | 6/2013 | Ogura |
| D684,686 S | 6/2013 | Cronenberg |
| D685,083 S | 6/2013 | Schneider |
| D685,084 S | 6/2013 | Guarraia |
| 8,465,455 B2 | 6/2013 | Cabiri |
| 8,469,942 B2 | 6/2013 | Kow et al. |
| D687,140 S | 7/2013 | Guarraia |
| D687,141 S | 7/2013 | Schneider |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| D687,536 S | 8/2013 | Guarraia |
| D688,784 S | 8/2013 | Schneider |
| 8,500,716 B2 | 8/2013 | Adair et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,545,469 B2 | 10/2013 | Andresen |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,613,719 B2 | 12/2013 | Karratt |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,632,499 B2 | 1/2014 | Grant et al. |
| 8,647,074 B2 | 2/2014 | Moberg et al. |
| 8,647,296 B2 | 2/2014 | Moberg et al. |
| 8,647,303 B2 | 2/2014 | Cowe |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| D702,834 S | 4/2014 | Norton et al. |
| 8,690,855 B2 | 4/2014 | Alderete et al. |
| 8,708,961 B2 | 4/2014 | Field et al. |
| 8,715,237 B2 | 5/2014 | Moberg et al. |
| 8,721,603 B2 | 5/2014 | Lundquist |
| 8,727,117 B2 | 5/2014 | Maasarani |
| 8,734,344 B2 | 5/2014 | Taub |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| D714,266 S | 9/2014 | Okamura |
| 8,845,587 B2 | 9/2014 | Lanigan et al. |
| D715,428 S | 10/2014 | Baid |
| 8,858,508 B2 | 10/2014 | Lavi et al. |
| 8,864,739 B2 | 10/2014 | Moberg et al. |
| 8,876,770 B2 | 11/2014 | Kraft et al. |
| 8,876,778 B2 | 11/2014 | Carrel |
| 8,882,711 B2 | 11/2014 | Saulenas |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| D722,870 S | 2/2015 | Fohner |
| 8,979,802 B2 | 3/2015 | Woehr |
| 8,986,250 B2 | 3/2015 | Beebe et al. |
| 9,011,164 B2 | 4/2015 | Filman et al. |
| 9,011,371 B2 | 4/2015 | Moberg et al. |
| 9,011,387 B2 | 4/2015 | Ekman et al. |
| 9,033,925 B2 | 5/2015 | Moberg et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,084,668 B2 | 7/2015 | Hamas |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat et al. |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| D745,661 S | 12/2015 | Collins |
| 9,205,188 B2 | 12/2015 | Lanigan et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| D751,699 S | 3/2016 | Mills |
| 9,283,327 B2 | 3/2016 | Hourmand et al. |
| D753,810 S | 4/2016 | Chang |
| 9,308,318 B2 | 4/2016 | Lanigan et al. |
| 9,308,319 B2 | 4/2016 | Mernoe |

(56) References Cited

U.S. PATENT DOCUMENTS

| | | |
|---|---|---|
| 9,308,327 B2 | 4/2016 | Marshall et al. |
| 9,314,569 B2 | 4/2016 | Causey et al. |
| 9,320,849 B2 | 4/2016 | Smith et al. |
| D755,950 S | 5/2016 | Meliniotis |
| 9,327,073 B2 | 5/2016 | Moberg et al. |
| 9,339,607 B2 | 5/2016 | Langley et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| D760,374 S | 6/2016 | Nagar |
| 9,364,606 B2 | 6/2016 | Cindrich et al. |
| 9,364,608 B2 | 6/2016 | Moberg et al. |
| 9,373,269 B2 | 6/2016 | Bergman |
| 9,381,300 B2 | 7/2016 | Smith et al. |
| 9,393,365 B2 | 7/2016 | Cabiri |
| D764,047 S | 8/2016 | Bjelovuk |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand et al. |
| 9,452,261 B2 | 9/2016 | Alon |
| D769,438 S | 10/2016 | Crosby |
| D770,037 S | 10/2016 | Schleicher |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,614 B2 | 11/2016 | Kamen |
| 9,492,622 B2 | 11/2016 | Brereton et al. |
| 9,498,573 B2 | 11/2016 | Smith |
| 9,522,234 B2 | 12/2016 | Cabiri |
| D776,262 S | 1/2017 | Tyce |
| D776,265 S | 1/2017 | Tyce |
| D777,331 S | 1/2017 | Jayalath |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,452 B2 | 2/2017 | Adair et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| D792,359 S | 7/2017 | Nakagawa |
| 9,707,356 B2 | 7/2017 | Hourmand et al. |
| D794,806 S | 8/2017 | Kranz |
| 9,744,306 B2 | 8/2017 | Cowe |
| D801,538 S | 10/2017 | Rondoni |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,827,369 B2 | 11/2017 | Cawthon |
| D806,232 S | 12/2017 | Hwang |
| 9,849,242 B2 | 12/2017 | Henley et al. |
| 9,862,519 B2 | 1/2018 | Deutschle et al. |
| D810,948 S | 2/2018 | Wielunski |
| D812,739 S | 3/2018 | Wolford |
| 9,999,722 B2 | 6/2018 | Yodfat et al. |
| 10,010,681 B2 | 7/2018 | Koch et al. |
| D825,356 S | 8/2018 | Yu |
| 10,076,356 B2 | 9/2018 | Hadvary et al. |
| 10,086,145 B2 | 10/2018 | Cabiri |
| D836,568 S | 12/2018 | Miller |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,048 B2 | 2/2019 | Gray et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | McLoughlin et al. |
| D847,976 S | 5/2019 | Protasiewicz |
| 10,369,289 B2 | 8/2019 | Cabiri |
| 10,376,641 B2 | 8/2019 | Hirschel et al. |
| 10,376,647 B2 | 8/2019 | Farris et al. |
| 10,398,832 B2 | 9/2019 | Qin |
| 10,434,262 B2 | 10/2019 | Bendek et al. |
| 10,500,352 B2 | 12/2019 | Grant et al. |
| 10,549,079 B2 | 2/2020 | Burton |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,646,643 B2 | 5/2020 | Cabiri |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,842,942 B2 | 11/2020 | Iibuchi et al. |
| 11,027,059 B2 | 6/2021 | Niklaus et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2002/0173748 A1 | 11/2002 | McConnell et al. |
| 2002/0173769 A1 | 11/2002 | Gray et al. |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0088238 A1 | 5/2003 | Poulsen |
| 2003/0125671 A1 | 7/2003 | Aramata et al. |
| 2003/0130618 A1 | 7/2003 | Gray et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0181868 A1 | 9/2003 | Swenson |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0003493 A1 | 1/2004 | Adair et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0254533 A1* | 12/2004 | Schriver ........... A61M 5/14546 604/131 |
| 2004/0260233 A1 | 12/2004 | Garibotto et al. |

(56) References Cited

U.S. PATENT DOCUMENTS

| | | |
|---|---|---|
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0064917 A1 | 3/2005 | Peng |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197626 A1 | 9/2005 | Moberg et al. |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0079767 A1* | 4/2006 | Gibbs ............... A61M 5/14546 600/432 |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0149921 A1 | 6/2007 | Michels |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0119794 A1 | 5/2008 | Alheidt |
| 2008/0119795 A1 | 5/2008 | Erskine |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0221523 A1 | 9/2008 | Moberg et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259143 A1 | 10/2009 | Bakhtyari-Nejad-Esfahani |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |

(56) References Cited

U.S. PATENT DOCUMENTS

| | | |
|---|---|---|
| 2010/0241065 A1 | 9/2010 | Moberg et al. |
| 2010/0241103 A1 | 9/2010 | Kraft et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0022464 A1 | 1/2011 | Dunn |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0166509 A1 | 7/2011 | Gross |
| 2011/0166512 A1 | 7/2011 | Both |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0288526 A1 | 11/2011 | Wei |
| 2011/0295205 A1 | 12/2011 | Kaufmann et al. |
| 2011/0313238 A1 | 12/2011 | Reichenbach et al. |
| 2011/0315269 A1 | 12/2011 | Williamson |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0109066 A1 | 5/2012 | Chase |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0138040 A1 | 5/2013 | Weinandy |
| 2013/0138078 A1 | 5/2013 | Smith |
| 2013/0153434 A1 | 6/2013 | Allanore |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0253472 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0310756 A1* | 11/2013 | Whalley ............ A61M 5/24 604/189 |
| 2013/0310807 A1 | 11/2013 | Adair et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128815 A1 | 5/2014 | Cabiri |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207067 A1 | 7/2014 | Kamen |
| 2014/0207104 A1 | 7/2014 | Vouillamoz et al. |
| 2014/0213975 A1 | 7/2014 | Clemente et al. |
| 2014/0214001 A1 | 7/2014 | Mortazavi |
| 2014/0228760 A1 | 8/2014 | Ethelfeld |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0296784 A1 | 10/2014 | Lopez |
| 2014/0330240 A1 | 11/2014 | Cabiri |
| 2014/0343503 A1 | 11/2014 | Holmqvist |
| 2014/0346378 A1 | 11/2014 | Kua |
| 2014/0350459 A1 | 11/2014 | Lanier, Jr. |
| 2014/0364808 A1 | 12/2014 | Niklaus et al. |
| 2015/0005703 A1 | 1/2015 | Hutchinson et al. |
| 2015/0011965 A1 | 1/2015 | Cabiri |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157786 A1 | 6/2015 | Sonderegger |
| 2015/0157788 A1 | 6/2015 | Gescheit |
| 2015/0157806 A1 | 6/2015 | Knutsson |

(56) References Cited

U.S. PATENT DOCUMENTS

| | | |
|---|---|---|
| 2015/0165121 A1 | 6/2015 | Murakami |
| 2015/0165129 A1 | 6/2015 | Row |
| 2015/0180146 A1 | 6/2015 | Filman |
| 2015/0202375 A1 | 7/2015 | Schabbach et al. |
| 2015/0250943 A1 | 9/2015 | Momose |
| 2015/0306307 A1 | 10/2015 | Cole |
| 2015/0359965 A1 | 12/2015 | O'Connor |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0058941 A1 | 3/2016 | Wu |
| 2016/0082184 A1 | 3/2016 | Hanagan |
| 2016/0089056 A1 | 3/2016 | Limaye |
| 2016/0121043 A1 | 5/2016 | Weibel |
| 2016/0135895 A1 | 5/2016 | Faasse |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0220755 A1 | 8/2016 | Lanigan et al. |
| 2016/0228652 A1 | 8/2016 | Cabiri et al. |
| 2016/0256352 A1 | 9/2016 | Bar-El |
| 2016/0256353 A1 | 9/2016 | Bar-El |
| 2016/0284239 A1 | 9/2016 | Bergman |
| 2016/0296699 A1 | 10/2016 | Cabiri |
| 2016/0296711 A1 | 10/2016 | Blancke |
| 2016/0296713 A1 | 10/2016 | Schader et al. |
| 2016/0296716 A1 | 10/2016 | Cabiri et al. |
| 2016/0317738 A1 | 11/2016 | Cross |
| 2016/0331900 A1 | 11/2016 | Wei |
| 2016/0339168 A1 | 11/2016 | Hutchinson et al. |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0021137 A1 | 1/2017 | Cole |
| 2017/0028132 A1 | 2/2017 | Cronenberg |
| 2017/0043092 A1 | 2/2017 | Murakami et al. |
| 2017/0058349 A1 | 3/2017 | Levy et al. |
| 2017/0080158 A1 | 3/2017 | Cabiri |
| 2017/0143907 A1 | 5/2017 | Stever |
| 2017/0175859 A1 | 6/2017 | Brockmeier |
| 2017/0224924 A1 | 8/2017 | Christensen |
| 2017/0246399 A1* | 8/2017 | Forlani ................ A61M 5/20 |
| 2017/0246403 A1 | 8/2017 | Cowe et al. |
| 2017/0340827 A1 | 11/2017 | Nazzaro |
| 2018/0028765 A1 | 2/2018 | Waller et al. |
| 2018/0071454 A1 | 3/2018 | Betts |
| 2018/0133413 A1 | 5/2018 | Grant et al. |
| 2018/0214637 A1 | 8/2018 | Kemp et al. |
| 2018/0304029 A1 | 10/2018 | Koch et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0099549 A1 | 4/2019 | Lanigan et al. |
| 2019/0110749 A1 | 4/2019 | Forrester |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0298921 A1 | 10/2019 | Stafford |
| 2019/0328968 A1 | 10/2019 | Giambattista |
| 2019/0358441 A1 | 11/2019 | Zvezdin |
| 2019/0381239 A1 | 12/2019 | Cabiri |
| 2020/0009323 A1 | 1/2020 | Nair et al. |
| 2020/0085349 A1 | 3/2020 | Bremer |
| 2020/0164151 A1 | 5/2020 | Farris et al. |
| 2020/0215270 A1 | 7/2020 | Ogawa et al. |
| 2020/0261643 A1 | 8/2020 | Boyaval |
| 2020/0297929 A1 | 9/2020 | Zhang |
| 2020/0316290 A1 | 10/2020 | Bourelle |
| 2020/0360602 A1 | 11/2020 | Gray et al. |
| 2020/0405951 A1 | 12/2020 | Burren |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1211454 | 3/1999 |
| CN | 1440301 | 9/2003 |
| CN | 1476566 A | 2/2004 |
| CN | 1486198 | 3/2004 |
| CN | 1505535 A | 6/2004 |
| CN | 1646180 A | 7/2005 |
| CN | 1747683 A | 3/2006 |
| CN | 1753699 | 3/2006 |
| CN | 1863564 | 11/2006 |
| CN | 1863566 A | 11/2006 |
| CN | 1951513 | 4/2007 |
| CN | 101090749 A | 12/2007 |
| CN | 101128228 | 2/2008 |
| CN | 101227943 A | 7/2008 |
| CN | 101448536 A | 6/2009 |
| CN | 101460207 A | 6/2009 |
| CN | 101461976 | 6/2009 |
| CN | 101522235 A | 9/2009 |
| CN | 101522239 | 9/2009 |
| CN | 101541362 A | 9/2009 |
| CN | 101641126 A | 2/2010 |
| CN | 101687075 | 3/2010 |
| CN | 101784297 | 7/2010 |
| CN | 101868273 A | 10/2010 |
| CN | 201692438 U | 1/2011 |
| CN | 102038998 | 5/2011 |
| CN | 102149416 | 8/2011 |
| CN | 201941304 U | 8/2011 |
| CN | 102186733 A | 9/2011 |
| CN | 102378638 A | 3/2012 |
| CN | 102438679 | 5/2012 |
| CN | 102458512 | 5/2012 |
| CN | 102464145 | 5/2012 |
| CN | 202236675 | 5/2012 |
| CN | 102648016 | 8/2012 |
| CN | 102711868 | 10/2012 |
| CN | 102971032 | 3/2013 |
| CN | 103025369 | 4/2013 |
| CN | 103118737 | 5/2013 |
| CN | 103228303 | 7/2013 |
| CN | 103619378 | 3/2014 |
| CN | 103648561 | 3/2014 |
| CN | 103702699 | 4/2014 |
| CN | 103732277 | 4/2014 |
| CN | 103764197 | 4/2014 |
| CN | 103921966 | 7/2014 |
| CN | 103974734 | 8/2014 |
| CN | 103998082 | 8/2014 |
| CN | 203874209 | 10/2014 |
| CN | 104411350 | 3/2015 |
| CN | 104487116 | 4/2015 |
| CN | 104519933 | 4/2015 |
| CN | 104619366 | 5/2015 |
| CN | 105102025 A | 11/2015 |
| CN | 205107679 | 3/2016 |
| CN | 105749383 | 7/2016 |
| CN | 107007910 | 8/2017 |
| DE | 0855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0851774 A1 | 7/1998 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |

(56) References Cited

FOREIGN PATENT DOCUMENTS

| | | |
|---|---|---|
| EP | 1923081 A2 | 5/2008 |
| EP | 1974759 A1 | 10/2008 |
| EP | 2007455 B1 | 12/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 1654018 | 11/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2593162 | 5/2013 |
| EP | 2719410 A2 | 4/2014 |
| EP | 2393535 B1 | 3/2015 |
| EP | 2878320 A1 | 6/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| EP | 3498320 A1 | 6/2019 |
| FR | 2770136 A1 | 4/1999 |
| GB | 2301035 | 11/1996 |
| GB | 2436526 A | 10/2007 |
| JP | 62-112566 A | 5/1987 |
| JP | S62112566 A | 5/1987 |
| JP | 01-172843 U | 12/1989 |
| JP | H01172843 U | 12/1989 |
| JP | 05-062828 A | 3/1993 |
| JP | H05062828 A | 3/1993 |
| JP | H05237188 | 9/1993 |
| JP | 07-194701 A | 8/1995 |
| JP | H07194701 A | 8/1995 |
| JP | 3035448 U | 3/1997 |
| JP | 09-505758 A | 6/1997 |
| JP | H1057489 | 3/1998 |
| JP | H1080486 | 3/1998 |
| JP | 11-507260 A | 6/1999 |
| JP | H11507260 A | 6/1999 |
| JP | 2000-107289 A | 4/2000 |
| JP | 2000190163 | 7/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 3098104 | 2/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007517589 | 7/2007 |
| JP | 2007518455 | 7/2007 |
| JP | 2007249805 | 9/2007 |
| JP | 2007-306990 A | 11/2007 |
| JP | 2008-534131 A | 8/2008 |
| JP | 2008-220961 A | 9/2008 |
| JP | 2008272084 | 11/2008 |
| JP | 2009-502273 A | 1/2009 |
| JP | 2009-101093 A | 5/2009 |
| JP | 2009205230 | 9/2009 |
| JP | 2009205342 | 9/2009 |
| JP | 2009539444 | 11/2009 |
| JP | 2010-501281 A | 1/2010 |
| JP | 2010-540054 A | 12/2010 |
| JP | 2010-540156 A | 12/2010 |
| JP | 2011509133 | 3/2011 |
| JP | 2011-136153 A | 7/2011 |
| JP | 2012023799 | 2/2012 |
| JP | 2012043553 | 3/2012 |
| JP | 2012059563 | 3/2012 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013516280 A | 5/2013 |
| JP | 2013517094 | 5/2013 |
| JP | D1441740 S | 5/2013 |
| JP | 2013-530778 A | 8/2013 |
| JP | 2013-531520 A | 8/2013 |
| JP | 2013-531540 A | 8/2013 |
| JP | 2013192637 | 9/2013 |
| JP | 2014-030489 A | 2/2014 |
| JP | 2014081861 | 5/2014 |
| JP | 2014-515669 A | 7/2014 |
| JP | 2014-518743 A | 8/2014 |
| JP | 2014-521443 A | 8/2014 |
| JP | 2014-525339 A | 9/2014 |
| JP | 2014211852 | 11/2014 |
| JP | 2015-514486 A | 5/2015 |
| JP | 2015128613 | 7/2015 |
| JP | 2016517262 | 6/2016 |
| JP | 2016-525428 A | 8/2016 |
| JP | 2016-530016 A | 9/2016 |
| JP | 2017045775 | 3/2017 |
| JP | 2018047239 | 3/2018 |
| JP | 2019003830 | 1/2019 |
| JP | 2019500720 | 1/2019 |
| KR | 300689248 S | 4/2013 |
| MX | PA06003233 | 6/2006 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 97/21457 A1 | 6/1997 |
| WO | 97/33638 A1 | 9/1997 |
| WO | 98/57683 A1 | 12/1998 |
| WO | 98/57686 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 00/69509 A1 | 11/2000 |
| WO | 01/30415 A2 | 5/2001 |
| WO | 01/30421 A2 | 5/2001 |
| WO | 0152920 A2 | 7/2001 |
| WO | 01/70304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 02/04049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |
| WO | 2004/000397 A1 | 12/2003 |
| WO | 2004/032990 A2 | 4/2004 |
| WO | 2004073554 A2 | 9/2004 |
| WO | 2004/098684 A2 | 11/2004 |

(56) References Cited

FOREIGN PATENT DOCUMENTS

| | | |
|---|---|---|
| WO | 2004/105841 A1 | 12/2004 |
| WO | 2005/018703 A2 | 3/2005 |
| WO | 2005/037350 A2 | 4/2005 |
| WO | 2005/070485 A1 | 8/2005 |
| WO | 2005/072795 A2 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |
| WO | 2007/017052 A1 | 2/2007 |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007106068 A2 | 9/2007 |
| WO | 2007/119178 A2 | 10/2007 |
| WO | 2007141210 A1 | 12/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009039013 A1 | 3/2009 |
| WO | 2009/043000 A1 | 4/2009 |
| WO | 2009/043564 A1 | 4/2009 |
| WO | 2009/044401 A2 | 4/2009 |
| WO | 2009/046989 A2 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011054160 | 5/2011 |
| WO | 2011/075105 A1 | 6/2011 |
| WO | 2011/090955 A1 | 7/2011 |
| WO | 2011/090956 A2 | 7/2011 |
| WO | 2011084951 A2 | 7/2011 |
| WO | 2011/101378 A1 | 8/2011 |
| WO | 2011/110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2011154160 A1 | 12/2011 |
| WO | 2012/003221 A1 | 1/2012 |
| WO | 2012007246 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013/036602 A1 | 3/2013 |
| WO | 2013/058697 A1 | 4/2013 |
| WO | 2013/115843 A1 | 8/2013 |
| WO | 2014049886 | 4/2014 |
| WO | 2014081411 A1 | 5/2014 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048791 A1 | 4/2015 |
| WO | 2015/048803 A2 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |
| WO | 2015/118358 A1 | 8/2015 |
| WO | 2015/163009 A1 | 10/2015 |
| WO | 2016/087626 A1 | 6/2016 |
| WO | 2016/087627 A1 | 6/2016 |
| WO | 2016/141082 A1 | 9/2016 |
| WO | 2016196934 | 12/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020023220 A1 | 1/2020 |
| WO | 2020/120087 A1 | 6/2020 |
| WO | 2020/193468 A1 | 10/2020 |

OTHER PUBLICATIONS

Office Action dated Nov. 6, 2015 in U.S. Appl. No. 14/715,791 by Cabiri.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.
Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.

(56) References Cited

OTHER PUBLICATIONS

European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Search Repport (Partial), dated Dec. 20, 2016 in Int'l Application No. PCT/US2016/056247.
Int'l Preliminary Report on Patentability dated Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Inte'l Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178319.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.

(56) References Cited

OTHER PUBLICATIONS

Office Action dated Dec. 9, 2016 in U.S. Appl. No. 14/593,051, by Gross.
Office Action dated Feb. 16, 2017 in CN Application No. 2014101783189.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 4, 2014 in EP Application No. 11 707 942.6.
Office Action dated Jan. 10, 2017 in U.S. Appl. No. 14/193,692, by Gross.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Amgen Inc., "The Neulasta Onpro Kit", http://www.neulastahcp.com/neulasta-onpro/, Copyright 2016, 16 pages.
BD Worldwide, "Self-Injection Systems", http://www.bd.com/pharmaceuticals/products/self-injection/patch-injectors.asp, Copyright 2017, 2 pages.
Int'l Preliminary Report on Patentability dated Jul. 10, 2019 in Int'l Application No. PCT/US2017/038527.
Int'l Preliminary Report on Patentability dated Jun. 25, 2020 in Int'l Application No. PCT/US2019/023646.
Int'l Preliminary Report on Patentability dated Feb. 12, 2021 in Int'l Application No. PCT/US2019/060740.
Int'l Search Report (Partial), dated Dec. 20, 2016 in Int'l Application No. PCT/US2016/056247.

(56) References Cited

OTHER PUBLICATIONS

Int'l Search Report and Written Opinion dated Jul. 22, 2019 in PCT Application No. PCT/US2019/023646.
Int'l Search Report and Written Opinion dated Feb. 17, 2020 in Int'l Application No. PCT/US2019/060740.
Office Action (Final Rejection) dated Mar. 16, 2023 for U.S. Appl. No. 17/395,670 (pp. 1-8).
Office Action dated Feb. 28, 2014 in CN Application No. 201180006571.0.
Office Action dated Mar. 2, 2018 in U.S. Appl. No. 29/597,876 by Norton.
Office Action dated Sep. 29, 2020 in JP Application No. 2018-538527.
Office Action dated Apr. 14, 2021 in EP Application No. 17734924.8.
Office Action dated Mar. 23, 2021 in JP Application No. 2019-543787.
OndrugDelivery, "Wearable Injectors", Sep. 19, 2016 Issue No. 70, 48 pages.
Reynolds, "Integrated Solutions for the Delivery of High-Volume Biologics", West Pharmaceutical Services, www.ondrugdelivery.com, Copyright 2014, 4 pages.
Sensile Medical AG, "SensePatch", https://www.sensile-medical.com/assets/data-sheet_5002_senspatch.pdf, 2017, 2 pages.
Unilife Corporation, "Wearable Injectors", http://www.unilife.com/product-platforms/WearableInjectors, Copyright 2016, 3 pages.
West Pharmaceutical Services, Inc. "SmartDose Platform" http://www.westpharma.com/products/self-injection-platforms/smartdoes, Copyright 2017, 3 pages.

\* cited by examiner

Figure 3
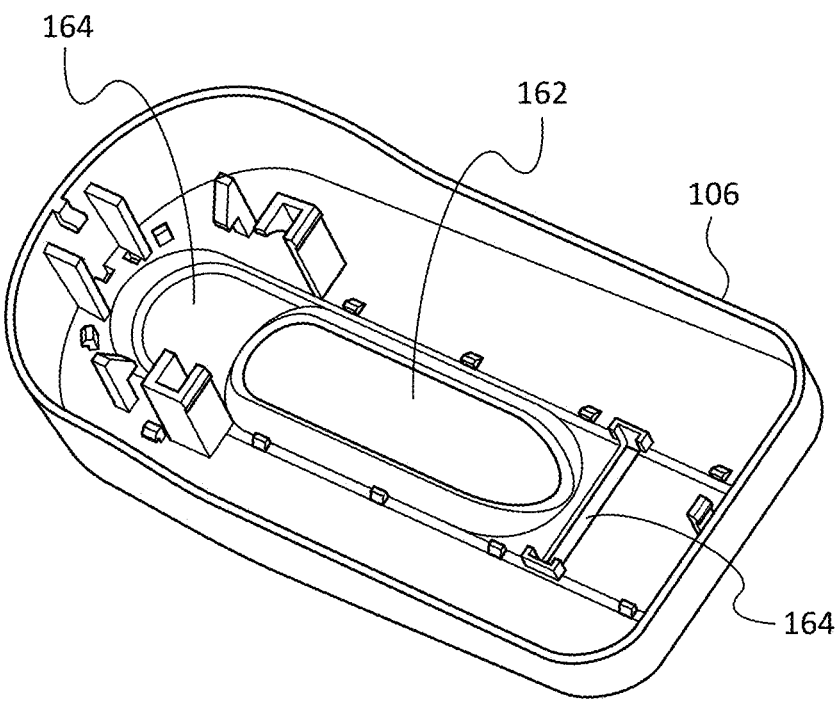
FIG. 3A
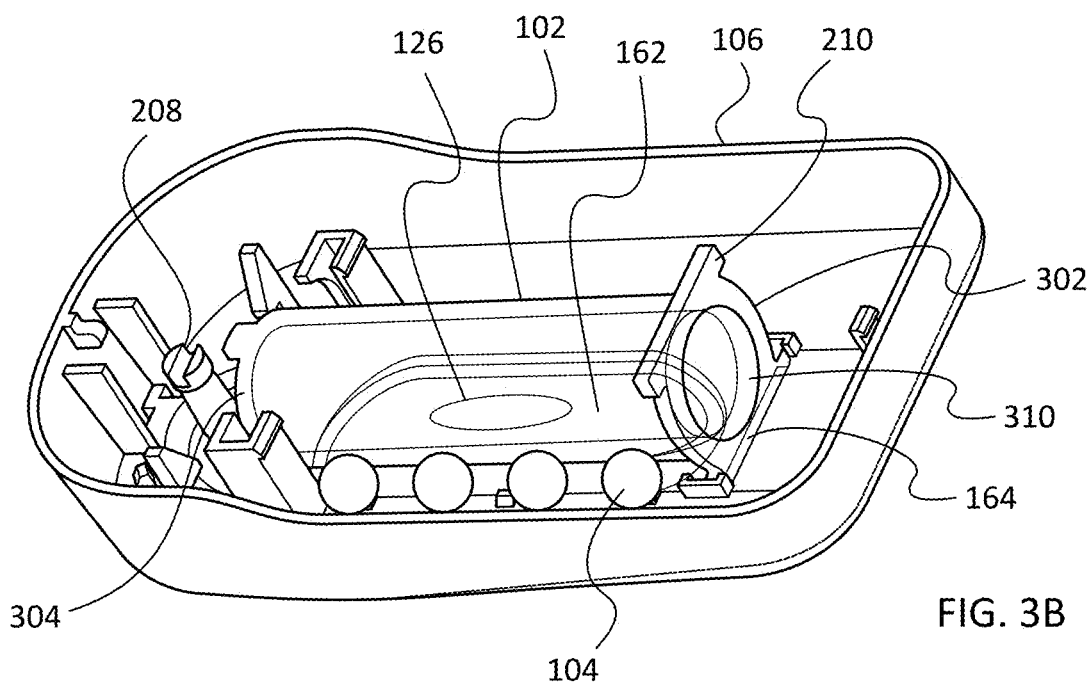
FIG. 3B

Figure 5
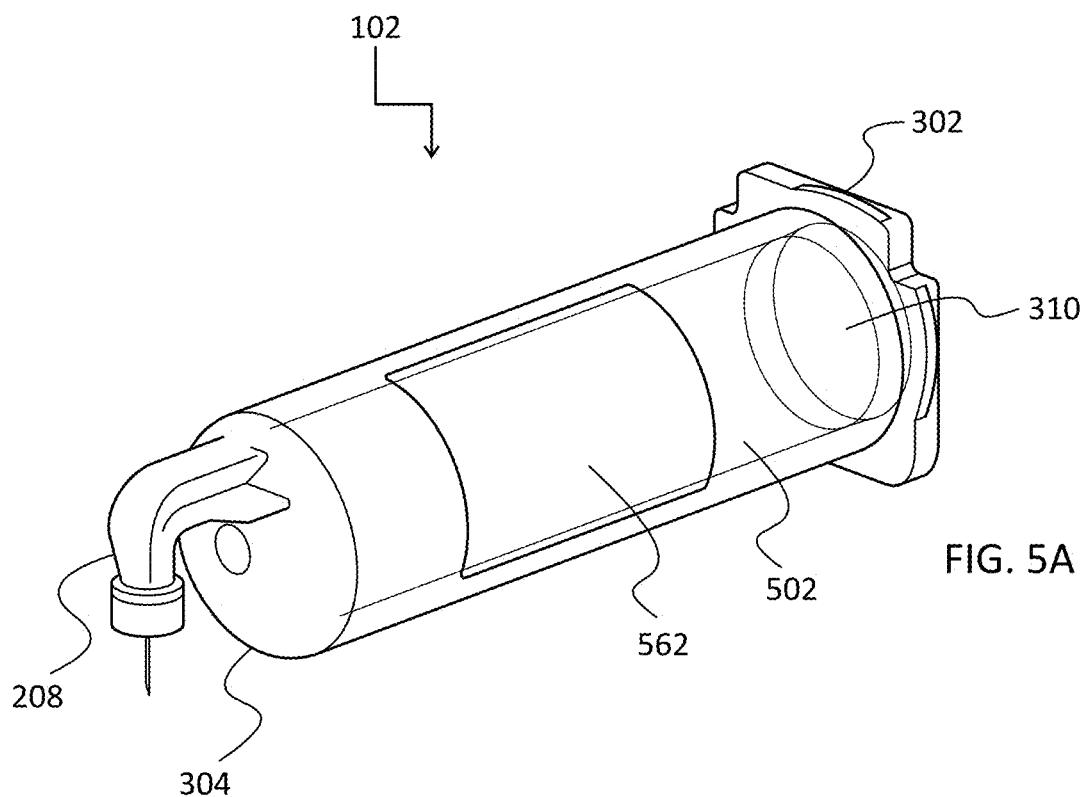
FIG. 5A
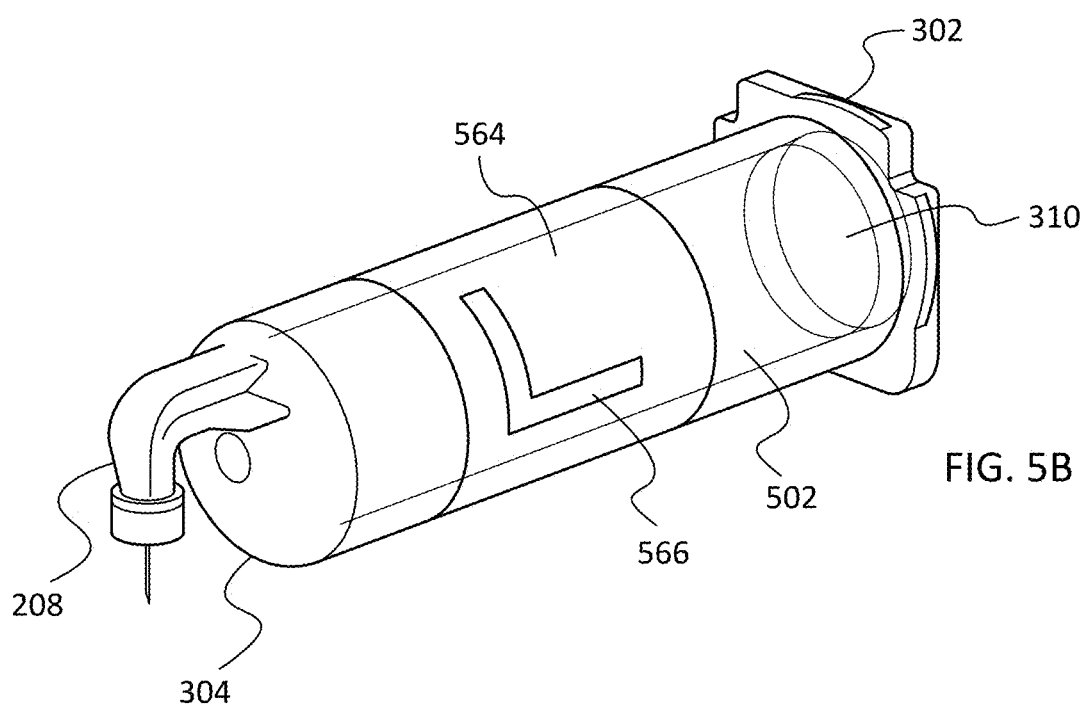
FIG. 5B

Figure 6
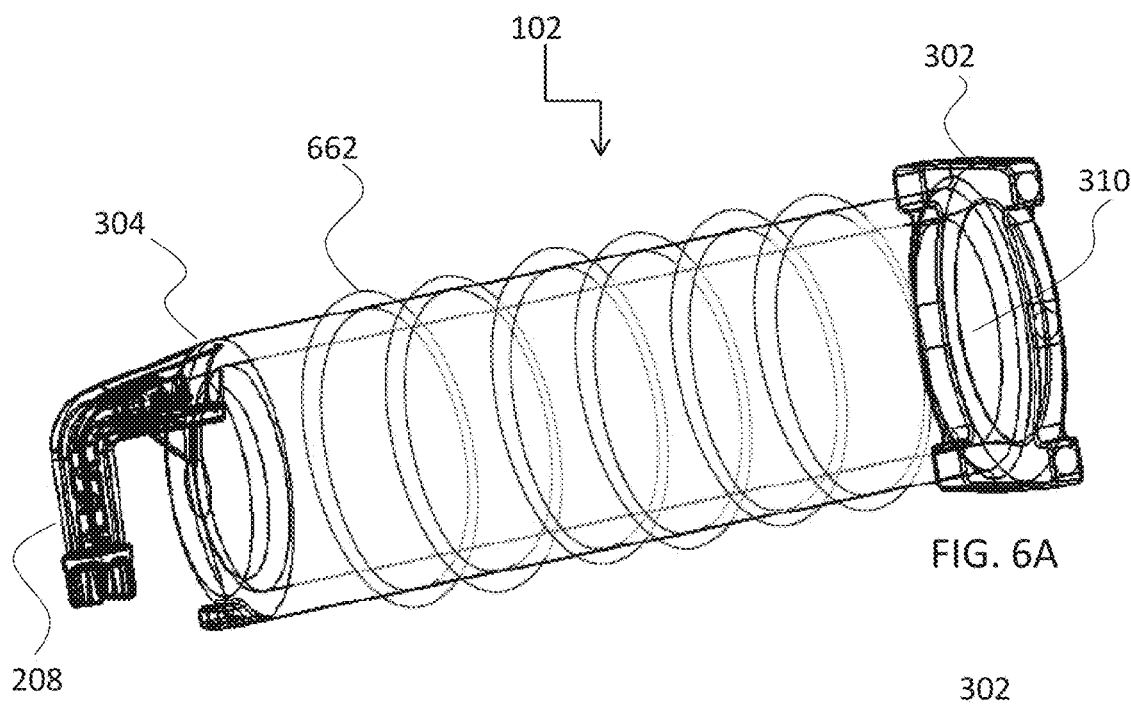
FIG. 6A
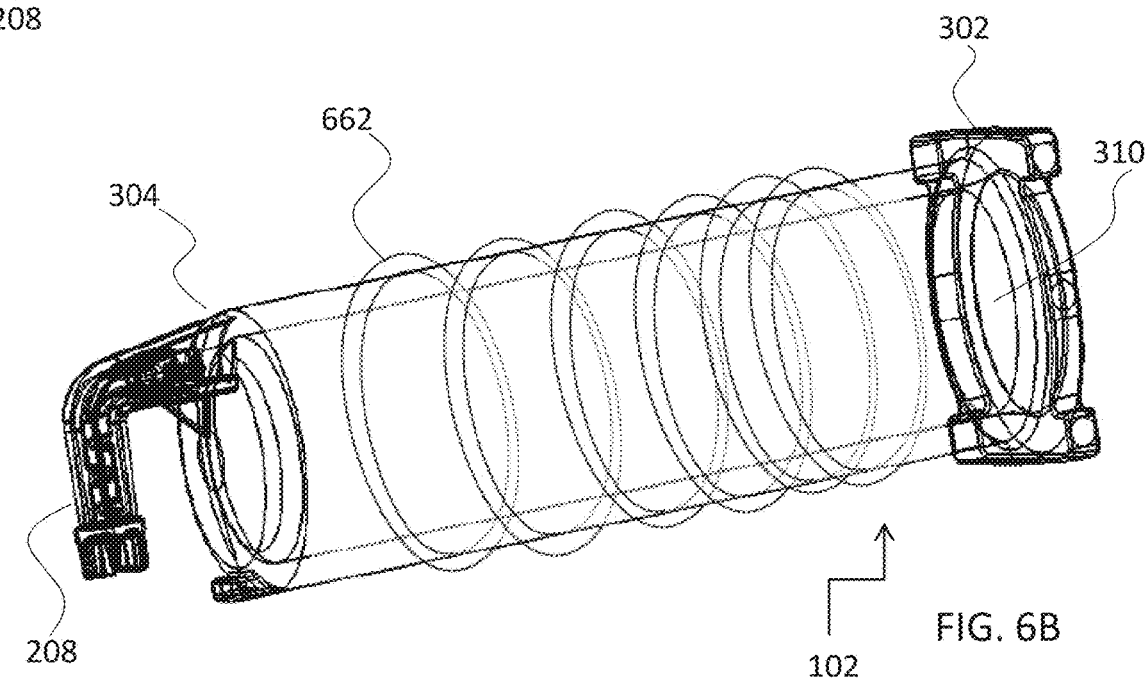
FIG. 6B

MEDICAMENT DELIVERY DEVICE COMPRISING A VISUAL INDICATOR

CROSS-REFERENCE TO RELATED APPLICATION SECTION

This application divisional of is a U.S. application Ser. No. 16/071,509, filed Jul. 20, 2018, which is a section 371 of International Application No. PCT/US2016/056258, filed Oct. 10, 2016, which was published Jul. 27, 2017 under International Publication No. WO 2017/127141 A1, which is a continuation of U.S. application Ser. No. 15/204,542, filed Jul. 7, 2016, which claims the benefit of U.S. Provisional Application No. 62/281,536, filed Jan. 21, 2016, and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to a visual user indicator and, more particularly, but not exclusively, to a medicament delivery device used as a user indicator light.

U.S. Pat. No. 8,784,378 discloses "A visual identification coding for a cartridge or cartridge holder for use with a drug delivery device is described. The visual identification coding includes a cartridge containing a drug and a light source located on the cartridge to visually indicate that the correct cartridge has been inserted into the drug delivery device. The light source may be a light emitting diode (LED), a surface mount diode (SMD), or an organic light emitting diode (OLED). A cartridge holder may also be included to receive the cartridge. In another embodiment, the light source may be located on the cartridge holder or a dose setting member."

U.S. Patent Application Publication no. 2014/0228768 to Eggert discloses "a handheld medical device having a housing, at least one operator activatable button mounted on a surface of the housing, and a light source mounted within the housing below the button and arranged to direct light towards the button. Substantially the whole of the button and the surface of the housing adjacent the button are opaque, save for a narrow strip adjacent the periphery of the button which is non-opaque."

Additional background art includes International Patent Application Publication no. WO2013173092 to the present inventor.

SUMMARY OF THE INVENTION

Example 1: A medical delivery device having a void for containing a cartridge and at least one window, comprising: a cartridge containing a fluid material, the cartridge including: a light pipe section which acts as a light pipe having an input location; and a light diffusing section optically coupled to the light pipe and aligned with the window when the cartridge is positioned in the void; a light source optically coupled to the cartridge at the input location to the light pipe, such that at least some light from the light source entering at the input location is diffused at the light diffusing section.

Example 2: A medical delivery device, comprising: a housing defining a void therein for a cartridge and having a window overlapping with at least part of the void; a cartridge containing a fluid material and positioned within the void, the cartridge including: a light pipe section which acts as a light pipe having an input location; and a light diffusing section optically coupled to the light pipe and aligned with the window when the cartridge is positioned in the void; a light source positioned within the housing and optically coupled to the cartridge at the input location to the light pipe, such that at least some light from the light source entering at the input location is diffused at the light diffusing section and exits the housing through the window.

Example 3: The device according to any of examples 1-2, further comprising a housing defining a void therein for the cartridge and having a window overlapping with at least part of the void; wherein the cartridge is positioned within the void, and the light source is positioned within the housing, such that the light diffused at the light diffusing section exits the housing through the window.

Example 4: The device according to any of examples 1-3, further comprising a control circuitry having instructions to operate the light source in accordance with an operation status of the medical delivery device.

Example 5: The device according to any of examples 1-2, wherein the light diffusing section comprises at least one protruding element.

Example 6: The device according to example 5, wherein the protruding element at least partially surrounds a circumference of the cartridge.

Example 7: The device according to example 5, wherein the protruding element extends at an angle beyond a tangent to a wall of the cartridge.

Example 8: The device according to example 1, wherein the light diffusing section comprises a surface area having increased surface roughness.

Example 9: The device according to example 8, wherein the surface area diffuses the light in an even distribution.

Example 10: The device according to example 8, wherein the surface area is sized to distribute the light over an area at least twice an area defined by a surface area of the light source.

Example 11: The device according to example 1, wherein the light diffusing section comprises at least one bulge.

Example 12: The device according to example 1, wherein the light diffusing section comprises at least one slit.

Example 13: The device according to example 1, wherein the cartridge further comprises indicia.

Example 14: The device according to example 13, wherein the light diffusing section is positioned in proximity to the indicia, such that the light pipe and the indicia are viewable from a single viewing direction.

Example 15: The device according to example 1, wherein the light source is provided at a number having a range of 2 to 7 light sources.

Example 16: The device according to example 1, wherein the light source is provided at a number having a range of 3 to 6 light sources.

Example 17: The device according to example 16, having a plurality of the input locations and a plurality of the light diffusing sections, each of which is coupled to each of the input locations.

Example 18: The device according to example 17, wherein each of the input locations and its associated light diffusing section are optically coupled to single light source of the light sources.

Example 19: A method for indicating a user about a state of a medical delivery device comprising: optically coupling at least one light source with a cartridge containing a fluid material and having a light input location; optically coupling through the cartridge a light diffusing section to the light input location; positioning the at least one light source and the cartridge in a housing having a window, such that the light diffusing section is aligned with the window; operating the at least one light source in accordance with a state of the medical delivery device.

Example 20: The method according to example 19, wherein the state of the medical delivery device comprises an ongoing delivery state.

Example 21: The method according to example 19, wherein the state of the medical delivery device comprises a stop delivery state.

Example 22: The method according to example 19, wherein the state of the medical delivery device comprises an on or off state.

Example 23: The method according to example 19, wherein the state of the medical delivery device comprises device malfunction state.

Example 24: The method according to example 19, wherein the state of the medical delivery device comprises an inventory status of the fluid material.

Example 25: The method according to example 19, wherein the operating the at least one light source comprises turning the light source in a continuous manner.

Example 26: The method according to example 19, wherein the operating the at least one light source comprises turning the light source on in an intermittent manner.

Example 27: The method according to example 26, wherein the operating the at least one light source comprises changing a frequency of the intermittent manner.

Example 28: The method according to example 19, wherein the operating the at least one light source comprises turning the light source off.

Example 29: The method according to example 19, wherein the operating the at least one light source comprises changing the light source color.

Example 30: A process of manufacturing a medical delivery device, comprising: molding a cartridge to include: a transparent section which acts as a light pipe having an input location; and a light diffusing section optically coupled to the light pipe; filling the cartridge with a fluid material; providing a housing defining a void therein for a cartridge and having a window overlapping with at least part of the void; positioning the cartridge within the void such that the light diffusing section is aligned with the window; positioning at least one light source within the housing and optically coupling the at least one light source to the light pipe through the input location, such that at least some light from the light source entering at the light pipe input is diffused at the light diffusing section and exits the housing through the window.

Example 31: The process according to example 30, wherein the molding comprises using Crystal Zenith.

Example 32: The process according to any of examples 30-31, further comprising operatively coupling the at least one light source with a control circuitry.

Example 33: The process according to example 32, further comprising programming the control circuitry to turn on or turn off the at least one light source according to an operation state of the device.

Example 34: The process according to example 32, further comprising programming the control circuitry to adjust a light generated by the at least one light source according to an inventory status of the fluid material.

Example 35: The process according to any of examples 30-34, further comprising molding the light diffusing section in a position allowing view of a physical indicator of an inventory state of the fluid material.

Example 36: The process according to example 35, wherein the physical indicator comprises a fluid level of the fluid material.

Example 37: The process according to example 35, wherein the physical indicator comprises indicia markings.

Example 38: The process according to example 35, wherein the physical indicator comprises a cartridge plunger position.

Example 39: A process of manufacturing a medical delivery device, comprising: molding a cartridge to include: a transparent section which acts as a light pipe having an input location; and a light diffusing section optically coupled to the light pipe; and filling the cartridge with a fluid material.

Example 40: The process according to example 30, further comprising: providing a housing defining a void therein for a cartridge and having a window overlapping with at least part of the void; positioning the cartridge within the void such that the light diffusing section is aligned with the window; positioning at least one light source within the housing and optically coupling the at least one light source to the light pipe through the input location, such that at least some light from the light source entering at the light pipe input is diffused at the light diffusing section and exits the housing through the window.

Example 41: The device according to example 1, further comprising a housing defining a void therein for the cartridge and having a window overlapping with at least part of the void; wherein the cartridge is positioned within the void, and the light source is positioned within the housing, such that the light diffused at the light diffusing section exits the housing through the window.

Example 42: The device according to example 1, further comprising a control circuitry having instructions to operate the light source in accordance with a status of the medical delivery device.

Example 43: The device according to example 1, wherein the light diffusing section comprises a surface area having increased surface roughness sized to distribute the light over an area at least twice an area defined by a surface area of the light source.

Example 44: The device according to example 1, wherein the cartridge further comprises indicia, and wherein the light diffusing section is positioned in proximity to the indicia, such that the light pipe and the indicia are viewable from a single viewing direction (possible for two windows or more).

Example 45: The method according to example 19, wherein the state of the medical delivery device comprises at least one of an ongoing delivery state, a stop delivery state, an on or off state, device malfunction state and any combination thereof.

Example 46: The method according to example 19, wherein the operating the at least one light source comprises turning the light source in a continuous manner or in an intermittent manner.

Example 47: The process according to example 30, further comprising operatively coupling the at least one light source with a control circuitry and programming the control circuitry to operate the at least one light source according to a state of the device.

Example 48: The process according to example 30, further comprising programming the control circuitry to adjust a light generated by the at least one light source according to an inventory status of the fluid material.

Example 49: The process according to example 30, further comprising molding the light diffusing section in a position allowing view of a physical indicator of an inventory state of the fluid material.

Example 50: A medical delivery device having a void for containing a cartridge and at least one window, comprising:
  (a) a cartridge containing a fluid material, wherein at least part of the cartridge is lined with a layer, the layer acts as a light pipe having a light input location, and the layer further comprises a light diffusing section optically coupled to the light pipe and aligned with the window when the cartridge is positioned in the void; and
  (b) a light source optically coupled to the layer at the input location to the light pipe, such that at least some light from the light source entering at the input location is diffused at the light diffusing section.

Example 51: The device according to example 50, wherein at least a portion of the layer comprises an adhesive surface for attaching onto a surface of the cartridge.

Example 52: The device according to example 50, wherein the layer is at least partially transparent.

Example 53: The device according to example 52, wherein the light diffusing section comprises at least one marking, the marking diffuses a limited range of wavelengths.

Example 54: The method according to Example 53, wherein the marking is text directed to a user indication of the device.

Example 55: The device according to Example 50, wherein the layer is configured to diffuse light having a wavelength selected according to at least one visual perceptive property of said fluid.

Example 56: A pharmaceutical delivery device comprising: a cartridge containing a fluid, the cartridge including: a light pipe section which acts as a light pipe having an input location; and a light diffusing section optically coupled to the light pipe; and a light source optically coupled to the cartridge at the input location to the light pipe, such that at least some light from the light source entering at the input location is diffused at the light diffusing section.

Example 57: The device according to Example 1, further comprising a housing defining a void therein for the cartridge and having at least one window, at least one of which overlapping with at least part of the void; wherein the cartridge is positioned within the void and the light source is positioned within the housing, such that the at least some light which is diffused at the light diffusing section, exits the housing through the window.

Example 58: The device according to any of Examples 1, 19, 30, 50, 56 and 57, wherein the fluid is a bioactive material.

Example 59: The device according to any of Examples 56-58, further comprising a control circuitry having instructions to operate the light source in accordance with a status of the pharmaceutical delivery device.

Example 60: The device according to any of Examples 56-59, wherein the light diffusing section comprises at least one protruding element.

Example 61: The device according to Example 60, wherein the protruding element at least partially surrounds a circumference of the cartridge.

Example 62: The device according to Example 60, wherein the protruding element extends at an angle beyond a tangent to a wall of the cartridge.

Example 63: The device according to any of Examples 56-62, wherein the light diffusing section comprises a surface area having increased surface roughness sized to distribute the light over an area at least twice an area defined by a surface area of the light source.

Example 64: The device according to any of Examples 56-63, wherein the cartridge further comprises indicia, and wherein the light diffusing section is positioned in proximity to the indicia, such that the light pipe and the indicia are viewable from a single viewing direction.

Example 65: The device according to any of Examples 56-64, wherein the light source is provided at a number having a range of 2 to 7 light sources.

Example 66: The device according to any of examples 56-65, wherein the light diffusing section is the cartridge wall.

Example 67: The device according to any of Examples 56-11, wherein the light diffusing section transmits 80% of the light from the light source.

Example 68: The device according to any of Examples 56-57, wherein the light diffusing section is a plunger provided in the cartridge.

Example 69: A method for indicating a user about a state of a pharmaceutical delivery device comprising: optically coupling at least one light source with a cartridge containing a fluid and having a light input location; optically coupling through the cartridge a light diffusing section to the light input location; positioning the at least one light source and the cartridge in a housing having at least one window, such that the light diffusing section is aligned with the at least one window; and operating the at least one light source in accordance with a state of the pharmaceutical delivery device.

Example 70: The method according to Example 69, wherein the state of the pharmaceutical delivery device comprises at least one of an ongoing delivery state, a stop delivery state, an on or off state, device malfunction state and any combination thereof.

Example 71: The method according to Example 69, wherein the state of the pharmaceutical delivery device comprises an inventory status of the fluid.

Example 72: The method according to any of Examples 69-71, wherein the operating the at least one light source comprises turning the light source in a continuous manner or in an intermittent manner.

Example 73: The method according to any of Examples 69-72, wherein the operating the at least one light source comprises changing the light source color.

Example 74: A process of manufacturing a pharmaceutical delivery device, comprising: forming a cartridge to include: a transparent section which acts as a light pipe having an input location; and a light diffusing section optically coupled to the light pipe; and filling the cartridge with a fluid.

Example 75: The process according to Example 19, further comprising: providing a housing defining a void therein for a cartridge and having a window overlapping with at least part of the void; positioning the cartridge within the void such that the light diffusing section is aligned with the window; positioning at least one light source within the housing and optically coupling the at least one light source to the light pipe through the input location, such that at least some light from the light source entering at the light pipe input is diffused at the light diffusing section and exits the housing through the window.

Example 76: The process according to Example 74, wherein the forming comprises molding.

Example 77: The process according to Example 76, wherein the molding comprises using Crystal Zenith.

Example 78: The process according to any of Examples 74-77, further comprising operatively coupling the at least one light source with a control circuitry and programming the control circuitry to operate the at least one light source according to a state of the device.

Example 79: The process according to Example 78, further comprising programming the control circuitry to adjust a light generated by the at least one light source according to an inventory status of the fluid.

Example 80: The process according to any of Examples 74-79, further comprising forming the light diffusing section in a position allowing view of a physical indicator of an inventory state of the fluid.

Example 81: A pharmaceutical delivery device having a void for containing a cartridge and at least one window, comprising: a cartridge containing a fluid, wherein at least part of the cartridge is lined with a layer, the layer acts as a light pipe having a light input location, and the layer further comprises a light diffusing section optically coupled to the light pipe and aligned with the window when the cartridge is positioned in the void; and a light source optically coupled to the layer at the input location to the light pipe, such that at least some light from the light source entering at the input location is diffused at the light diffusing section.

Example 82: The device according to Example 81, wherein at least a portion of the layer comprises an adhesive surface for attaching onto a surface of the cartridge.

Example 83: The device according to any of Examples 81-82, wherein the layer is at least partially transparent.

Example 84: The device according to Example 83, wherein the light diffusing section comprises at least one marking, the marking diffuses a limited range of wavelengths.

Example 85: The method according to Example 84, wherein the marking is text directed to a user indication of the device.

Example 86: The device according to any of Examples 81-85, wherein the layer is configured to diffuse light having a wavelength selected according to at least one visual perceptive property of the fluid.

Example 87: A cartridge for positioning within a pharmaceutical delivery device having a housing, the cartridge comprising: a light pipe section which acts as a light pipe having an input location; and a light diffusing section optically coupled to the light pipe; wherein the light diffusing section extends beyond a plane defined by the housing.

Example 88: The cartridge according to Example 87, wherein when the input location is optically coupled to a light source, at least some light from the light source entering at the input location is diffused at the light diffusing section.

Example 89: The cartridge according to any of Examples 87-88, wherein the cartridge and the light diffusing section are made from the same material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-B schematically illustrate an exemplary drug delivery device housing in accordance with some embodiments of the current invention, wherein FIG. 3A illustrates a perspective view of a housing cross section and FIG. 3B illustrates a perspective view of a housing cross section and an optional cartridge in accordance with some embodiments of the current invention;

FIGS. 5A-B schematically illustrates a perspective view of an exemplary cartridge having an optional light diffusing surface and/or sticker, in accordance with some embodiments of the current invention, wherein FIG. 5A illustrates a light diffusing surface and FIG. 5B illustrates a light diffusing sticker;

FIGS. 6A-B schematically illustrate a perspective view of an exemplary cartridge having optional light diffusing protrusions, in accordance with some embodiments of the current invention, wherein FIG. 6A illustrates protrusions arranged equidistantly, and FIG. 6B illustrates protrusions arranged in a non-equidistant manner;

DESCRIPTION OF SPECIFIC EMBODIMENTS OF THE INVENTION

Figure 1:
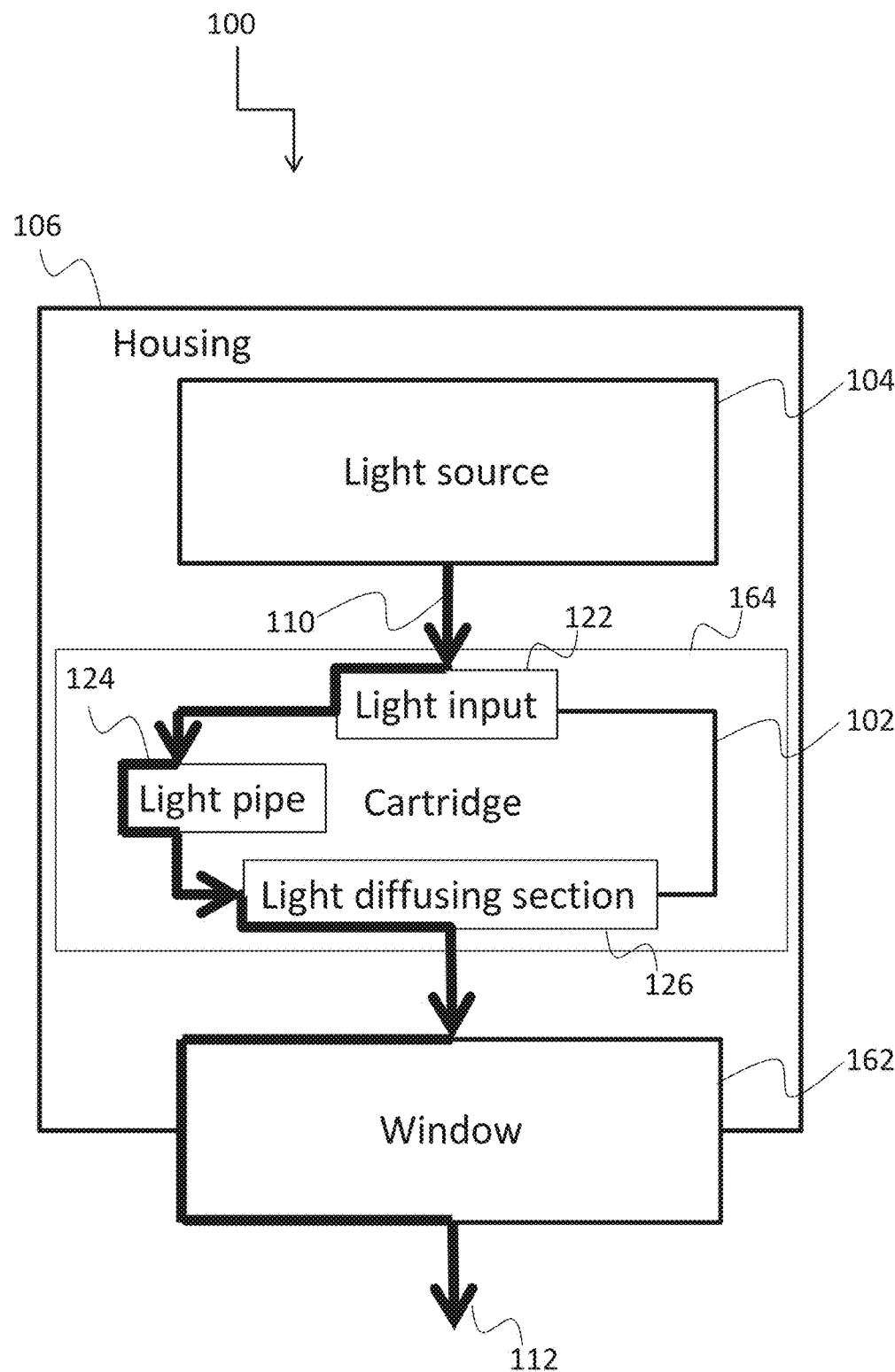
FIG. 1 is block diagram illustrating an exemplary device having a user indicator light in accordance with some embodiments of the current invention.

The present invention, in some embodiments thereof, relates to a visual user indicator and, more particularly, but not exclusively, to a medicament delivery device used as a user indicator light.

Overview

An aspect of several embodiments of the invention relates to using a cartridge as a light pipe for indicating a status of a pharmaceutical delivery device. In some embodiments, a light pipe refers to light traveling and/or diffusing and/or being transmitted and/or guided in at least a portion of a volume of a cartridge wall, the cartridge optionally containing a medicament, e.g. a bioactive material. For example, a bioactive material is any composition having a therapeutic effect on a patient's body. Alternatively, a medicament is a non-bioactive material, such as for example, placebo. In some embodiments, the cartridge comprises a light diffusing section, e.g. an element being optically coupled to the light pipe and serving to diffuse light out of the cartridge wall. Alternatively or additionally, a light diffusing section acts as a light input, collecting light form a light source and into the cartridge pipe light. Optionally, such a cartridge is being used as a user indicator module in a drug delivery device, such as for example an injector device.

As used herein, a cartridge is a compartment containing fluid, and having a needle. In some embodiments, the needle is parallel with respect to the longitudinal axis of the cartridge. Alternatively, the needle is bent with respect to the longitudinal axis of the cartridge, optionally being substantially perpendicular to it. Fluid, as used herein, refers to a liquid and/or gas used for medical purposes. In some embodiments, fluid includes a medicament, optionally a bioactive material such as a drug, or a non-bioactive material such as a placebo. In some embodiments, fluid includes a suspension, and/or a solution, and/or a mixture of miscible or immiscible liquids.

In some embodiments, a light source is optically coupled to the cartridge, wherein at least some of the light generated by the light source is transmitted and/or guided and/or diffuses and/or travels across at least a portion of the volume of the cartridge wall. In some embodiments, a light source is optically coupled to the cartridge by a light diffusing section positioned on the cartridge such that it is embedded within the injector device; optionally the light diffusing section is not viewable from outside a housing containing the cartridge and only serves as a light input location. Alternatively or additionally, a light diffusing section optically coupled to light traveling in the cartridge, is positioned on the cartridge in a position which is viewable from outside a housing containing the cartridge.

For example, light generated by the light source travels to a light diffusing section embedded in the injector device and serving as a light input, and the light input guides the light to travel through at least a portion of the volume of the cartridge. Optionally, a second light diffusing section, optionally positioned substantially opposite to the light input, guides the light traveling through the volume of the cartridge to be viewable from the opposite direction of the cartridge. Alternatively or additionally, light diffuses through the fluid contained in the cartridge.

In some embodiments, at least two windows are provided in an injector housing, optionally for allowing a user to view more than one portion of the cartridge. Optionally, at least one window allows viewing of the medicament and/or plunger. Alternatively or additionally, at least one window allows viewing of the light diffusing section. In some embodiments, the same window allows viewing of both the medicament (and/or plunger) and the light diffusing section. A potential advantage of having a window to view the medicament, through which light is also transmitted, is that light generated within the injector assists in improving the inspection of the medicament status in the injector.

In some embodiments, light is generated by the light source in accordance with a state of a delivery cartridge device. In some embodiments, state is an operation status of the device, for example an ongoing delivery state and/or a stop-delivery state and/or an end-of-delivery state and/or an on/off state of a motor and/or availability of an electricity source and/or device malfunction. Alternatively or additionally, state is an inventory status of the amount of fluid delivered and/or left in the cartridge.

A potential advantage of using a medicament cartridge to transmit a user indicator light is reducing the need to add a separate module of an indicator light to a delivery device. Reducing the number of modules in a device is likely to reduce possible malfunctions of the device. In addition, another potential advantage is an enlarged surface area exhibiting the indicator light, which is likely to be viewable from a wide range of viewing angles. Usually the delivery cartridge surface visible by a user is larger than the typical indicator light provided in a separate module, and therefore, a user may detect the indicator light with greater ease and by looking from many different angles. In some embodiments, most of the light generated within the device comes out of the cartridge, e.g. at least 90%, or at least 80% or at least 70%, or at least 60%.

In some embodiments, a light source positioned in proximity to a cartridge containing a medicament serves a double role: a first role comprises being a status indicator light configured to travel through at least a portion of the cartridge wall and be in a viewing path of a user. A second role comprises lighting the cartridge content, enabling viewing of the medicament status in the cartridge, and/or viewing of indicia provided on the cartridge wall and/or viewing of a plunger position. In some embodiments, using the same window, a user can see an indication light of the status of the device operation simultaneously with observing the status of the medicament, such as for example the fluid level of the medicament, and/or the plunger position, and/or indicia markings. A potential advantage of having the same observation window for the above indication is that it gives a user a redundant view of two indicators possibly reducing the probability of misinterpretation and/or providing to the user an indicator of when there is a malfunction in one of the indicators. In some embodiments, at least two windows are provided, at least one for viewing at least the medicament and at least one for viewing at least a cartridge light guide. Optionally, both windows are positioned to enable viewing at the same time.

In some embodiments, the same light source illuminates the cartridge (potentially facilitating reading of the graduation and/or the level of medicine) and/or includes a coded status indicator (e.g. color and/or flickering). In some embodiments, light properties are suitable to a light traveling characteristic of the medicament, e.g. different light features are used if the medicament is opaque, or transparent or translucent. In some embodiments, the color of the light source is determined in accordance with a medicament color. In some embodiments, the medicament can be a material having any color. Alternatively or additionally, the medicament can have a milky and/or opaque appearance.

In some embodiments, a plunger configured for facilitating the medicament, provides a change in the total reflection of the light traveling through the cartridge wall, optionally causing light to diffuse out of the cartridge wall to a direction of a user, at the point where the plunger edge contacts the cartridge wall, providing a light indication of the plunger position. Alternatively or additionally an optical element (for example a diffuser and/or a reflector) may be added to the plunger, for example at the base (e.g. the proximal end) of the plunger. Alternatively or additionally, a wall of the plunger being in contact with the cartridge can serve as a light guide.

In some embodiments, a housing is provided having an observation window enabling a user to view a delivery cartridge serving as a light pipe embedded in the housing. Optionally, an observation window is any aperture in a housing containing a delivery cartridge and enabling a user a visual view of the cartridge. In some embodiments, the observation window is provided for a user visual detection of an indicator light embedded inside the housing and having a light path to the cartridge. Optionally, the observation window serves as a visual indicator of a light produced inside the housing traveling across a volume of the cartridge. Potentially the observation window is doubly used for the detection of an indicator light and for a user visual inspection of the cartridge content. Alternatively or additionally, the cartridge is provided with an appendage having light transmitting and/or diffusing properties. Optionally an observation window may include a pane and/or may include an open space.

In some embodiments, operation status is indicated by using a plurality of light wave properties, for example, frequency and/or amplitude and/or duration. In some embodiments, light is transmitted continuously. Alternatively or additionally, light is transmitted intermittently, for example by flickering. In some embodiments, light properties include frequency of flickering, which might increase or decrease over time. For example, flickering frequency, in some embodiments, is correlated to the delivery speed and/or is correlated with a medicament amount having been delivered.

In some embodiments, the cartridge serves as a pipe light by having at least a portion of a transparent section. As used herein, transparent relates to a material allowing at least some traveling of light therethrough. In some embodiments the cartridge comprises a light diffusing section in the form of an appended visual feature. In some embodiments, the visual feature is configured to guide (i.e. transmit) a light path through it. Alternatively or additionally, the visual feature is configured to diffuse light through it. In some embodiments, the visual feature protrudes from the surface of the cartridge, optionally made of the same material as the cartridge, optionally molded with the outer surface of the cartridge. Alternatively, the visual feature is in a different composition than the cartridge and is designed to guide and/or diffuse light around at least a partial circumference of the cartridge.

In some embodiments the visual feature comprises a plurality of protrusions, for example circumferential protruding ribs and/or segments of circumferential protruding ribs, optionally orthogonal to the longitudinal axis of the cartridge. Alternatively or additionally, the visual feature comprises a plurality of spaced apart bulges. A potential advantage of a surface having protrusions thereon is that protruding elements are likely to transmit and/or diffuse a greater amount of light with respect to a smooth surface. In some embodiments the protrusions are equidistant, probably enabling substantial uniform transmission of light. Alternatively, the protrusions are asymmetrically distributed, probably enabling more light to transmit to a predefined surface region.

Alternatively or additionally, the visual feature comprises a plurality of slots and/or grooves. Alternatively or additionally, the visual feature comprises at least one protrusion and at least one slot. Potentially, either protrusions and/or slots are configured to make light traveling through the volume of the cartridge's wall to diffuse outside of the cartridge wall. Alternatively or additionally, at least a portion of the cartridge wall comprises increased roughness, causing light to diffuse out of the cartridge wall. In some embodiments, surface textures such as bulges and/or slots and/or roughness are provided on the outer surface of the cartridge wall. Alternatively or additionally, surface textures are provided on the inner surface of the cartridge wall.

In some embodiments, protrusions are arranged in a group, guiding a light path from an individually operated light source. Optionally, a plurality of such groups is provided, each being coupled to a distinctly operated light source. A potential advantage of multiple individually operated groups is the increase of visual information provided to the user simultaneously, by having a different interpretation assigned to each group of protrusions. For example, a first group of protrusions is linked to a first light source indicating, e.g., the delivery operation state of the device, and a second group of protrusions is linked to a second light source indicating e.g., the state of the medicament amount.

In some embodiments the visual feature comprises a projecting element having light guiding and/or diffusing properties. In some embodiments, the element is projected beyond a plane defined by the cartridge and/or the housing. A potential advantage of a light transmitting projecting element is its likelihood to better guide a propagation of light through it. In addition, a protruding element is likely to be seen and/or noticed more conveniently from a variety of observation angles.

In some embodiments, a projecting element includes a light diffusing section configured to extend beyond a plane defined by the housing of cartridge and/or a plane defined by the inner edge of a window and/or a plane defined by an outer edge of a window. A potential advantage of extending beyond the housing and/or the edge of the window is an increase in a user available viewing angles of the light diffusing section. In some embodiments, more than one light diffusing section is provided, optionally each being coupled to a different light source.

In some embodiments the cartridge comprises at least one alignment guide defining an orientation of the cartridge with respect to an embedding injector device. In some embodiments, the alignment guide projects beyond the outer surface of the cartridge. Alternatively, the alignment guide comprises a recess in the outer surface of the cartridge. Optionally, the alignment guide interlocks with a complementary geometrical feature within the injector device, optionally preventing rotation of the cartridge with respect to the device. Potentially, alignment guides enable positioning of the cartridge at a predefined orientation, for example with respect to the observation window of the device housing and/or a light source, optionally allowing an appended visual feature to be visible to a user.

An aspect of several embodiments of the invention relates to a process of manufacturing a light transmitting and/or diffusing cartridge for medicament delivery to serve as a user indicator module, used for example in an injector device.

In some embodiments, a drug delivery device is provided by embedding a cartridge in a housing having a window at least partially aligned with the cartridge position. Optionally, the window follows a cartridge's longitudinal axis, or any axis across which a medicament is expelled.

In some embodiments, at least one light source is positioned within said housing such that it is optically coupled to the cartridge. In some embodiments a range of 1 to 10 light sources is provided. Alternatively a range of 2 to 7 light sources is provided. Alternatively, a range of 3 to 6 light sources are provided. Alternatively 4 light sources are provided.

In some embodiments a cartridge is manufactured from a material which permits traveling of electromagnetic waves in a visible frequency range. Optionally, the material is at least partially transparent, optionally providing view of the composition being delivered. Alternatively, the cartridge is internally coated with an opaque material, such as for example in the case of a light-sensitive medicament, but the cartridge wall enables visible light to diffuse across its volume. In some embodiments, at least part of the cartridge is manufactured using Crystal Zenith, optionally by molding. Alternatively or additionally, at least part of the cartridge is manufactured using glass. Alternatively or additionally, at least part of the cartridge is manufactured using a standard material known in the art to be used for cartridges.

In some embodiments the cartridge is molded asymmetrically, optionally having transmitting/diffusing elements where an observation window is designed to be fit with respect to the cartridge. Alternatively or additionally, the cartridge is molded having transmitting/diffusing elements which are embedded inside the injector housing, optionally not viewable from the outside. Alternatively or additionally, the cartridge is molded to have a defined angle with respect to the observation window and housing plane.

In some embodiments, the cartridge is manufactured from layers having at least two materials. Optionally, at least one of the layering materials is opaque. Alternatively or additionally, at least one of the layering materials is transparent, optionally partially. In some embodiments, in at least one of the layers visible light travels and/or diffuses throughout its volume.

An aspect of some embodiments of the invention relates to a light guiding liner and/or sticker sized and shaped to line at least a portion of a medicament cartridge. In some embodiments, the sticker comprises a material having light diffusing properties, i.e. light can travel and/or diffuse and/or be transmitted through at least a portion of the volume of the sticker. Optionally, at least a portion of the sticker surface comprises an adhesive material for adhering onto a cartridge inner and/or outer surface. In some embodiments, the sticker includes text and/or markings over it surface, optionally visible only when being exposed to light being in a particular wavelength range.

Optionally, the sticker is visible only when sharing a visual path with a light having a wavelength in the range of 400-450, and/or 450-480, and/or 480-490 and/or 490-500, and/or 500-560, and/or 560-580, and/or 580-600, and/or 600-650 and/or 650-750, and/or any range larger, smaller or intermediate range.

In some embodiments, the text and/or markings comprise a light diffusing material and are lit once light travels to them from a light input location. Optionally, the sticker comprises a light input located inside an injector housing, and sharing a visual path with at least one light source embedded within the housing. Alternatively or additionally, text and/or markings are visible by having only a contour which is a light guiding material. Alternatively or additionally, the text and/or markings are visible by being surrounded by a light guiding sticker and not guiding light themselves, such as by punching the text and/or markings out of the sticker and creating a material-free space being in the shape of the text and/or markings.

In some embodiments, the cartridge and/or syringe is manufactured in a process distinct from the filling of the fluid reservoir. Accordingly, optionally, some light guide types are provided in the first process and other light guide types are provided in the second process. For example, molded light guide features may be provided through the molding process of the cartridge, while the liner may be assembled onto the cartridge by a different manufacturer, either before or after filling and/or sealing with the plunger. In some embodiments, the light guide features provided by the first process are configured to be compatible to a variety of light sources and/or fluids. Alternatively or additionally, the light guide features provided by the second process are specifically tailored to the specific fluid type and/or light properties of the fluid being used for filling. Optionally, the features in the first process are provided independently from the features in the second process.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary User Indicator Light Path for Use in a Drug Delivery Device

Referring now to the drawings, FIG. 1 illustrates a block diagram illustrating an exemplary device having a user indicator light in accordance with some embodiments of the current invention. In some embodiments, a drug delivery device is provided with a housing 106 having a window 162, and having a void 164. In some embodiments, a cartridge 102 containing a medicament, e.g. a bioactive material, is positioned within void 164. In some embodiments, a light source 104 is also positioned within the housing, optionally in proximity to the cartridge.

In some embodiments, cartridge 102 is configured to serve as a light pipe, bridging light generated by light source 104 to window 162. Optionally, cartridge 102 comprises a light input location 122 sharing an optical pathway with the light source 104. In some embodiments, cartridge 102 is made of a material having light propagating properties. Optionally at least a portion of the wall of cartridge 102, serves as a light pipe 124 for transmitting light at least through a portion of its volume.

Figure 4:
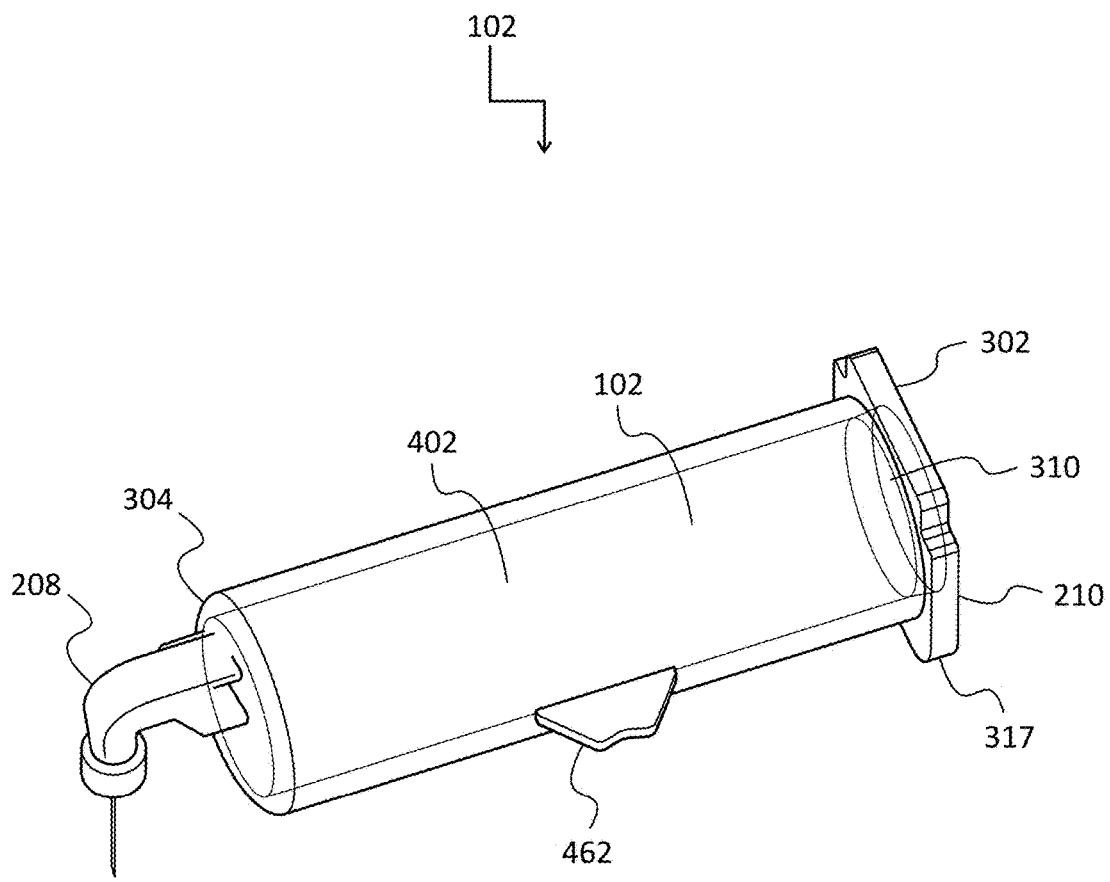
FIG. 4 schematically illustrates a perspective view of an exemplary cartridge having an optional extended light diffusing section, in accordance with some embodiments of the current invention.

In some embodiments, cartridge 102 comprises a light diffusing section 126. Optionally, light diffusing section 126 comprises an extending element. Optionally, the extending element is substantially perpendicular to a longitudinal axis of cartridge 102, as shown for example in FIG. 4. Alternatively or additionally, light diffusing section 126 comprises a plurality of protruding elements as shown for example in FIG. 6. Alternatively or additionally, light diffusing section 126 comprises at least one bulge as shown for example in FIG. 7. Alternatively or additionally, light diffusing section 126 comprises at least one slot as shown for example in FIG. 8. Alternatively or additionally, light diffusing section 126 comprises at least one surface area having an increased roughness relative to other portions of the cartridge 102 as shown for example in FIG. 5. In some embodiments, the distal portion of the cartridge comprises a flange which serves as a light diffusing section 126, as shown in FIG. 4.

In some embodiments, light diffusing section 126 comprises an arrangement along a longitudinal axis of the cartridge. Alternatively or additionally, light diffusing section 126 comprises an arrangement along at least a portion of the cartridge circumference. In some embodiments, light pipe 124 comprises a material extending along at least a portion of the cartridge 102 circumference, serving as a light pipe between a light source positioned in proximity to one portion of the light pipe, to a light diffusing section positioned in proximity to a second portion of the light pipe.

In some embodiments, light generated by light source 104 travels through light path 110. Optionally, light generated by light source 104 travels to light input 122 found in cartridge 102. In some embodiments, light travels from light input 122 into the light pipe 124 of cartridge 102. Optionally, light pipe 124 includes a transparent section of cartridge 102. In some embodiments, light pipe 124 comprises the entire volume of the wall of cartridge 102. Alternatively, only a portion of cartridge 102 is made of a material enabling light traveling. In some embodiments, cartridge 102 comprises layers of materials, at least one of which allows light to travel through it.

In some embodiments, light traveling through light path 110 is internally reflected except for when encountering light diffusing section 126. In some embodiments, light diffusing section 126 is shaped to allow light traveling through light path 110 to diffuse out of the internal volume of cartridge 102.

In some embodiments, window 162 is aligned with cartridge 102 such that light diffusing section 126 is viewable through window 162. As such, in some embodiments, light traveling through light path 110 diffuses out of light diffusing section 126 and out 112 of housing 106.

In some embodiments, window 162 is positioned in a top cover of housing 106, optionally near the position of an operation button. Alternatively or additionally, window 162 is positioned in a base of housing 106, optionally near a position of a removable safety liner.

In some embodiments, window 162 is shaped as a circle. Alternatively or additionally, window 162 is shaped as an ellipse or an elongated polygon, optionally aligned with a longitudinal axis of cartridge 102. Alternatively or additionally, window 162 is shaped as a slot.

In some embodiments, housing 106 comprises a plurality of windows 162, optionally aligned with different segments of cartridge 102. Alternatively or additionally, window 162 includes a viewing section in-between a plurality of housing compartments. For example, if housing 106 is provided in a multi-part configuration, the plurality of housing parts are optionally assembled such that at least a portion of cartridge 102 can be viewed in between the housing parts. Optionally, cartridge 102 serves as a connector between pluralities of housing parts, for example, by having at least one housing for a proximal end of the cartridge and a separate at least one housing for the distal end of the cartridge, while at least a portion of the middle section of the cartridge is available for viewing in between the proximal and distal housing compartments.

Exemplary Drug Delivery Device Having a Cartridge Used as a Light Pipe

Figure 2:
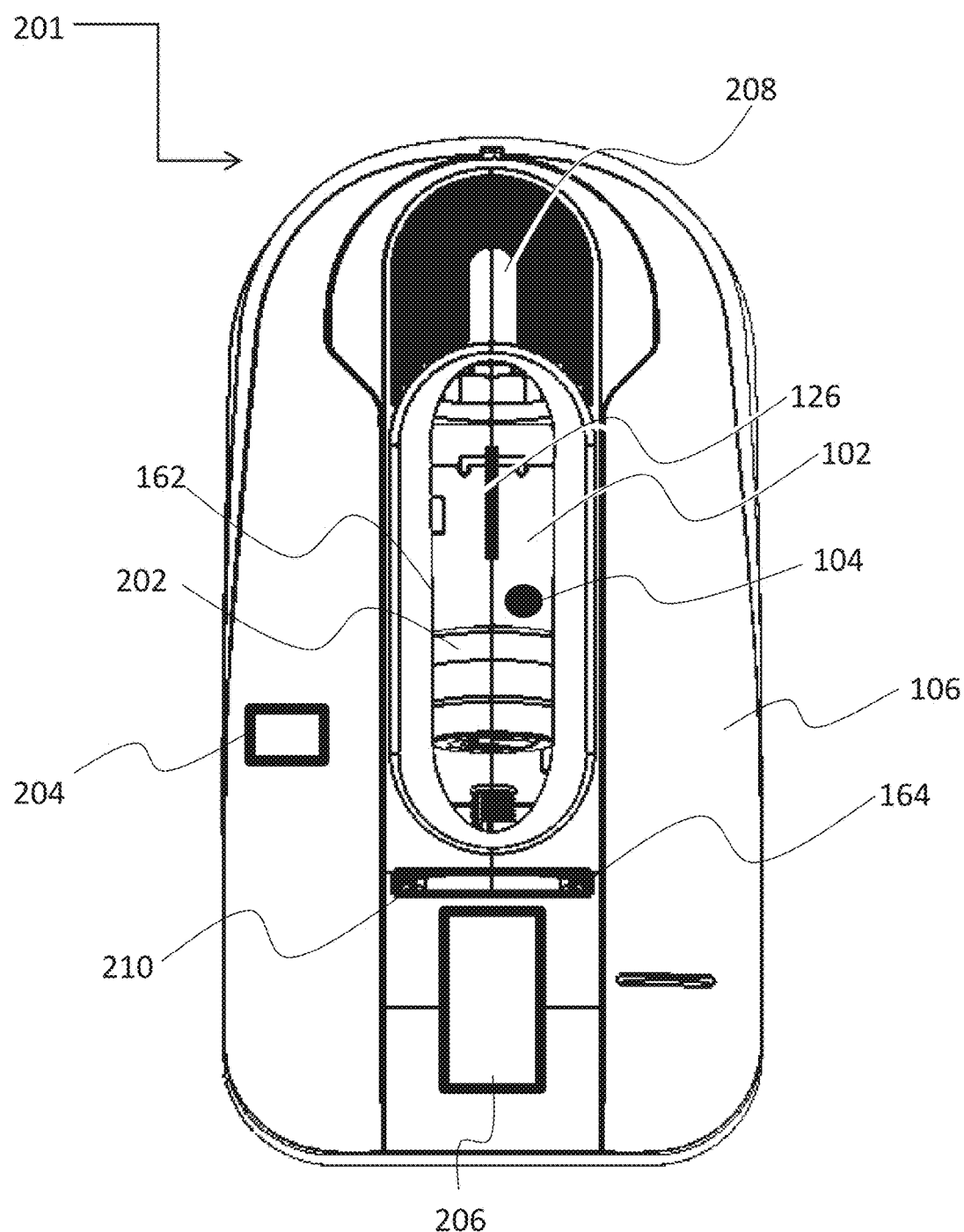
FIG. 2 schematically illustrates a top view of an exemplary drug delivery device having a user indicator light in accordance with some embodiments of the current invention.

Reference is now made to FIG. 2, schematically illustrating a top view of an exemplary drug delivery device having a user indicator light in accordance with some embodiments of the current invention. In some embodiments, a cartridge 102 is used as a user indicator of a drug delivery device, for example injector 201. According to some embodiments, injector 201 comprises a housing 106 having a window 162, aligned with a cartridge 102. The cartridge 102, in some embodiments, is positioned such that a light diffusing section 126 is viewable through window 162. In some embodiments, light diffusing section 126 diffuses light, originally transmitted from cartridge 102, which serves as a light pipe from light source 104.

In some embodiments, light diffusing section 126 is found on the dorsal side of the cartridge, i.e. the side that faces window 162. In such embodiments, light diffusing section 126 is optionally used to transmit light diffusing through the walls of cartridge 102. Alternatively or additionally, light diffusing section is found on the ventral side of the cartridge, i.e. the side that faces the inner portion of injector 201. In such embodiments, light diffusion section 126 optionally serves as a light input, collecting light generated inside injector 201 by light source 104, and transmitting the light to the cartridge walls, a light which is then viewable through window 162. In some embodiments, window 162 comprises a dome, e.g. a curved material and/or cylindrically shaped cover, for covering and/or protecting the cartridge. A potential advantage of providing a curved covering is in protecting light diffusion section 126 if it extends beyond the surface of housing 106. Typically, a protective cover is useful when the cartridge and/or light diffusing section 126 are made of glass and prone to break if receiving a shock. In some embodiments, the dome projects from a plane defined by the surface of the housing by at least 0.5 mm, and/or at least 1 mm, and/or at least 2 mm, and/or at least 5 mm.

In some embodiments, window 162 serves a second role when allowing viewing of plunger 202, which is configured to push a medicament out of cartridge 102 through a fluid outlet, located at location 208. Optionally, plunger 202 is pushed by motor 206. Alternatively or additionally, window 162 allows viewing of the medicament fluid level found in cartridge 102. Alternatively, cartridge 102 comprises an inner layer which is opaque, for protecting light sensitive medicaments.

In some embodiments, a control circuitry 204 is provided, optionally having instructions to operate light source 104. For example, control circuitry 204 in some embodiments can get input from motor 206 as to an operation state of the device, and optionally accordingly provide instructions for light generation by light source 104. Alternatively or additionally, control circuitry 204 in some embodiments can get input as to a plunger 202 position, and optionally accordingly provide instructions for light generation by light source 104.

Optionally, housing 106 comprises at least two windows 162 and 164. In some embodiments, window 164 allows viewing of the distal portion 302 of cartridge 102. Optionally, the distal portion of cartridge 102 comprises a light diffusing section in the form of a flange 210, which is further illustrated in detail in FIG. 3. In some embodiments, window 164 is sized and shaped to allow viewing of the flange, the window optionally being in the shape of a slot.

Exemplary Drug Delivery Device Housing and Cartridge

Reference is now made to FIG. 3, schematically illustrating an exemplary drug delivery device housing in accordance with some embodiments of the current invention, wherein FIG. 3A illustrates a perspective view of a housing cross section, and FIG. 3B illustrates a perspective view of a housing cross section and accommodating a cartridge in accordance with some embodiments of the current invention.

In some embodiments, a drug delivery device, such as for example an injector, comprises a housing 106 having a window 162. In some embodiments, housing 106 comprises a void 164 sized and shaped to accommodate a cartridge 102. Optionally, window 162 is provided in accordance with the void 164 such that the cartridge 102 is at least partially viewable from the window. In some embodiments, the portion of the cartridge viewable from the window is configured to serve as a user indicator light, optionally by including in the viewable portion a light diffusing section 126.

In some embodiments, cartridge 102 comprises a proximal end 304 defined by having a needle accommodating member 208, and a distal end 302 defined by having a bore 310 for accommodating a plunger. In some embodiments, plunger is configured to be pushed along a longitudinal axis of cartridge 102, optionally, being aligned with the longitudinal axis of window 164. In some embodiments, non-symmetric orientation features of the cartridge lead to positioning of the cartridge such that the distal end 302, proximal end 304 and the light diffusing section 126 are correctly aligned with housing 106 and/or window 162. For example, interlocking members could be provided in cartridge 102 and housing 106. In some embodiments, such non-symmetric orientation alignment features keep cartridge 102 from shifting and/or rotating within housing 106. Alternatively or additionally, a distal and/or proximal end of the cartridge includes a connector, such as for example a septum and/or a physical connecting feature, e.g. a snap and/or a circumferential lip.

In some embodiments, light source 104 is positioned in housing 106 such that it shares an optical pathway with at least a portion of cartridge 102, optionally with a portion comprising a transparent section for allowing light to travel through a volume of cartridge 102, optionally through its wall. In some embodiments, more than one light source is provided, optionally more than 2. Alternatively, more than 3 light sources are provided. Alternatively more than 4 light sources are provided. In some embodiments, each light source is optically coupled to a different light pipe provided in cartridge 102, and/or optically coupled to a different light diffusing section. In some embodiments, a plurality of light sources is provided to enhance the viewing area of the indication light, optionally having all light sources operated in the same manner. Alternatively, a plurality of light sources is provided to allow different indications operated simultaneously, for example, a green light indicates operating status of the device motor and it is simultaneously turned on together with a blinking red light indicating delivery. In some embodiments, light source 104 comprises a light emitting diode.

Exemplary Cartridge Having an Extended Light Diffusing Section

Reference is now made to FIG. 4, schematically illustrating a perspective view of an exemplary cartridge having at least one extended light diffusing section, in accordance with some embodiments of the current invention.

In some embodiments, light diffusing section 462 is provided to diffuse light traveling in light pipe 402, optionally being a wall of cartridge 102. In some embodiments, light pipe 402 comprises the entire wall of cartridge 102 extending from distal portion 302 to proximal portion 304. Alternatively, light pipe 402 is provided by having a transparent section only in a portion of cartridge 102, optionally, only a portion of a longitudinal axis. Alternatively, light pipe 402 is provided by having a transparent section only in a portion of cartridge 102, optionally, only a portion of a circumference of the cartridge 102.

In some embodiments, light diffusing section 462 extends at an angle beyond a plane being tangent to the circumference of cartridge 102. Alternatively or additionally, light diffusing section 462 extends to a direction perpendicular to the longitudinal axis of cartridge 102. In some embodiments, light diffusing section 462 comprises a longitudinal axis substantially aligned with the longitudinal axis of cartridge 102. Alternatively, light diffusing section 462 comprises a longitudinal axis substantially perpendicular to the longitudinal axis of cartridge 102.

In some embodiments, section 462 is molded with the cartridge in a molding process. Alternatively or additionally, section 462 is added to the cartridge, optionally by providing section 462 to be sized and shaped to fit at least a portion of the cartridge. In some embodiments, section 462 is pressed against the light transmitting wall/layer of the cartridge.

Optionally, the distal end 302 of cartridge 102 comprises a flange 210. In some embodiments, flange 210 serves as a light diffusing section, in addition to or instead of light diffusing section 462. In some embodiments, flange 210 comprises an edge at least partially surrounding the perimeter of distal end 302, optionally having at least one brim feature 317 extending beyond the perimeter of distal end 302 in a direction away from the central axis of cartridge 102. Potentially, brim feature 317 can guide light generated by light source comprised in the housing, and optionally deliver the light through flange 210. In some embodiments, at least a portion of flange 210 delivering the light is viewable from outside the housing. Alternatively or additionally, flange 210 and/or brim 317 are sized and shaped to complement at least one feature comprised in the housing, potentially fixing an orientation of the position of the cartridge within the housing.

A potential advantage of guiding light through a light diffusing section provided in the distal end 302 of cartridge 102 is that the distal end region is potentially free of medicament, which is probably located in a more proximal position of the cartridge, after the plunger. An environment without medicament potentially allows light to diffuse without interference or altering effects, which might be caused by a presence of a medicament.

Exemplary Cartridge Having a Light Diffusing Surface Area

Reference is now made to FIG. 5A, schematically illustrating a perspective view of an exemplary cartridge having at least one light diffusing surface area, in accordance with some embodiments of the current invention.

In some embodiments, light diffusing surface area 562 is provided in cartridge 102. In some embodiments, surface area 562 is configured to diffuse light traveling through light pipe 502 provided by cartridge 102 by having a rough surface. In some embodiments, a rough surface is defined as a surface which is not tangential to the cartridge circumference and/or extending in a variety of angles, optionally without order. In some embodiments, the greater the angles of the non-tangential surfaces, the greater the roughness level is defined. Potentially, light traveling through light pipe 502 is internally reflected when encountering a smooth surface and/or diffuses out of the light pipe when encountering rough surface 562.

In some embodiments, more than one rough surface area 562 is provided. In some embodiments, surface area 562 is configured to diffuse light in an even manner, i.e. diffuse equal portions of light per area unit. Alternatively, surface area 562 is configured to provide unequal portions of light to diffuse per area unit, for example, by having a gradient of roughness level and/or areas of greater/smaller roughness level.

Reference is now made to FIG. 5B, schematically illustrating an aspect of some embodiments of the invention of providing a cartridge 102 with liner and/or sticker 564. In some embodiments, cartridge 102 is lined with sticker 564 on its inner surface. Alternatively or additionally, sticker 564 is lined over the outer surface of cartridge 102. In some embodiments, sticker 564 comprises a material having light guiding properties, and optionally, light generated inside an injector housing shares a visual path with sticker 564.

In some embodiments, sticker 564 comprises at least one marking 566, which is optionally text and/or indicia and/or a symbol and/or any other visual mark. Optionally, marking 566 is only visible when a shared-path light is generated within the injector housing. In some embodiments, marking 566 is only visible when the light generated inside has a particular range of wavelengths, for example, being in the range of 400-450, and/or 450-480, and/or 480-490 and/or 490-500, and/or 500-560, and/or 560-580, and/or 580-600, and/or 600-650 and/or 650-750, and/or any range larger, smaller or intermediate range. In some embodiments, an adhesive layer and/or a sticker has a thickness in the range of about 0.05 mm to about 1 mm. Alternatively, a thickness is in a range of 0.25 mm to about 0.75 mm.

Optionally, marking 566 is visible sharing a visual path with an inner light source, while the surrounding sticker 564 does not guide light through it. Alternatively or additionally, marking 566 and surrounding sticker 564 guide light having different wavelength ranges. Alternatively or additionally, only surrounding sticker 564 guides light, while marking 566 does not, such as for example, by punching out the area being taken by and/or the outline surrounding marking 566. In some embodiments, marking 566 is printed on the sticker before its placement onto the cartridge. In some embodiments, marking 566 comprises text, optionally directed to a user indication of the device, such as for example, indicating "OK" and/or "Error" if the device malfunctions, and/or "Cold". User indicating text is optionally provided to a user using a different color, or a different range of wavelengths, for each user indicating text. For example, "Error" may be indicated with a red light and/or provided with a red filter, "OK" may be presented as green and "Cold" may be presented with blue.

In some embodiments, sticker 564 is flexible. Optionally, sticker 564 can be lined over any commercially available cartridge. In some embodiments, sticker 564 is lined over at least a portion of a cartridge which has been manufactured by molding, after the molding process is done, optionally before cartridge 102 is filled with a medicament. Alternatively, sticker 564 is lined over cartridge 102 after the cartridge is filled. In some embodiments, at least part of sticker 564 is transparent. Alternatively or additionally, at least part of sticker 564 is semi-transparent. Alternatively or additionally, at least part of sticker 564 is opaque.

In some embodiments, sticker 564 is configured to transmit light having a particular range of wavelengths. The wavelength transmitted by sticker 564 is optionally selected according to at least one visual perceptive property of the medicament comprised in the cartridge. In some embodiments, a visual perceptive property comprises the color of the medicament. Alternatively or additionally, the visual perceptive property includes the reflectivity of the medicament. Alternatively or additionally, the visual perceptive property includes the absorbance of the medicament.

Exemplary Cartridge Having Light Diffusing Protruding Elements

Reference is now made to FIG. 6, schematically illustrating a perspective view of an exemplary cartridge having a plurality of light diffusing protrusions, in accordance with some embodiments of the current invention, wherein FIG. 6A illustrates protrusions arranged equidistantly, and FIG. 6B illustrates protrusions arranged in a non-equidistant manner.

In some embodiments, at least one protruding element 662 is provided, extending along at least a portion of a circumference of cartridge 102. In some embodiments, a plurality of protruding elements 662 is provided. Optionally, the protruding elements 662 are arranged equidistantly, optionally along a longitudinal axis of cartridge 102. A potential advantage of equidistant elements 662 is a uniform view from a variety of viewing angles. Alternatively, protruding elements 662 are arranged non-equidistantly, optionally with respect to a longitudinal axis of cartridge 102. A potential advantage of non-equidistant elements 662 is for example allowing viewing the medicament being delivered at a portion having elements 662 being more distant from each other.

Exemplary Cartridge Having a Light Diffusing Bulge

Figure 7:
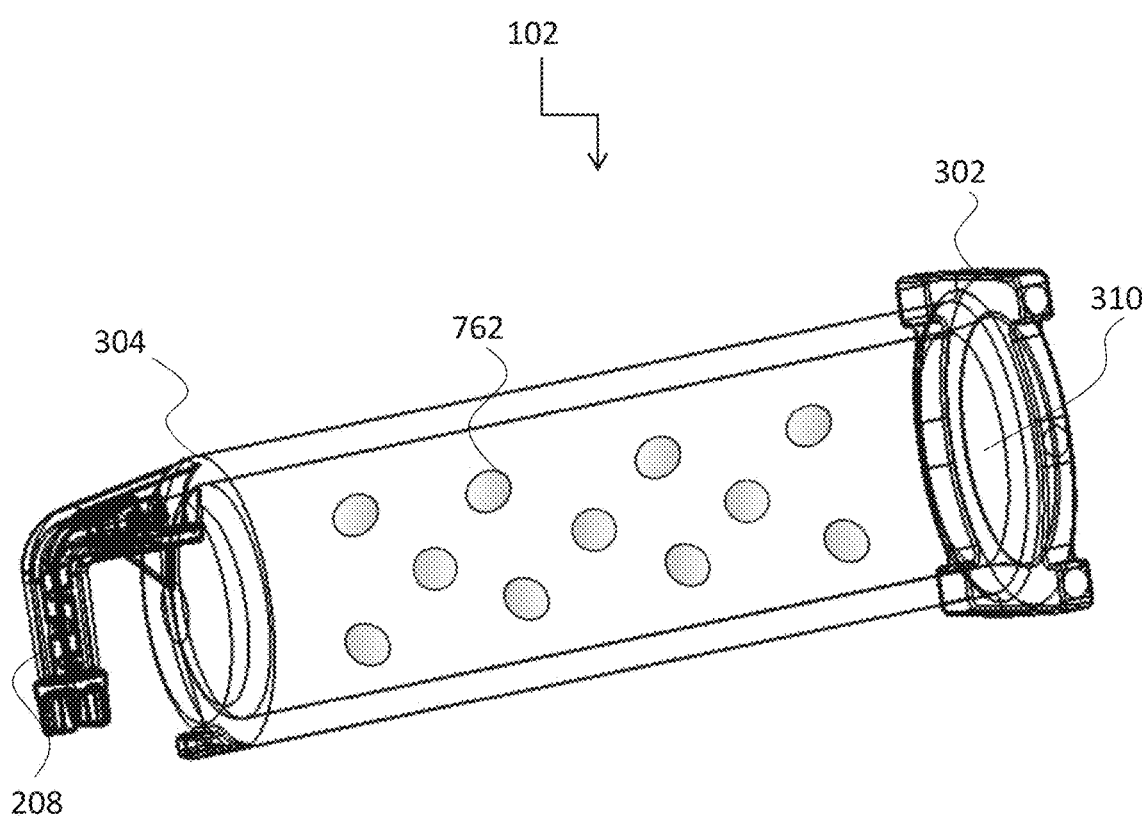
FIG. 7 schematically illustrates a perspective view of an exemplary cartridge having an optional light diffusing bulge, in accordance with some embodiments of the current invention.

Reference is now made to FIG. 7, schematically illustrating a perspective view of an exemplary cartridge having at least one light diffusing bulge, in accordance with some embodiments of the current invention.

In some embodiments, light diffusing section of cartridge 102 comprises at least one bulge 762. In some embodiments, bulge 762 comprises a protruding surface limited to a relatively small surface area. In some embodiments, a bulge 762 protrudes from a section area being in a range of about 1% to about 5% of the entire surface area of the cartridge 102. Alternatively or additionally, a bulge 762 protrudes from a section area being in a range of about 10% to about 20% of the entire surface area of the cartridge 102. Alternatively or additionally, a bulge 762 protrudes from a section area being in a range of about 20% to about 30% of the entire surface area of the cartridge 102.

In some embodiments, a bulge 762 extends to a height being no more than 0.2 mm. Alternatively or additionally, bulges 762 extend to a height being no more than 0.5 mm. Alternatively or additionally, bulges 762 extend to a height being no more than 1 mm.

Exemplary Cartridge Having a Light Diffusing Slot

Figure 8:
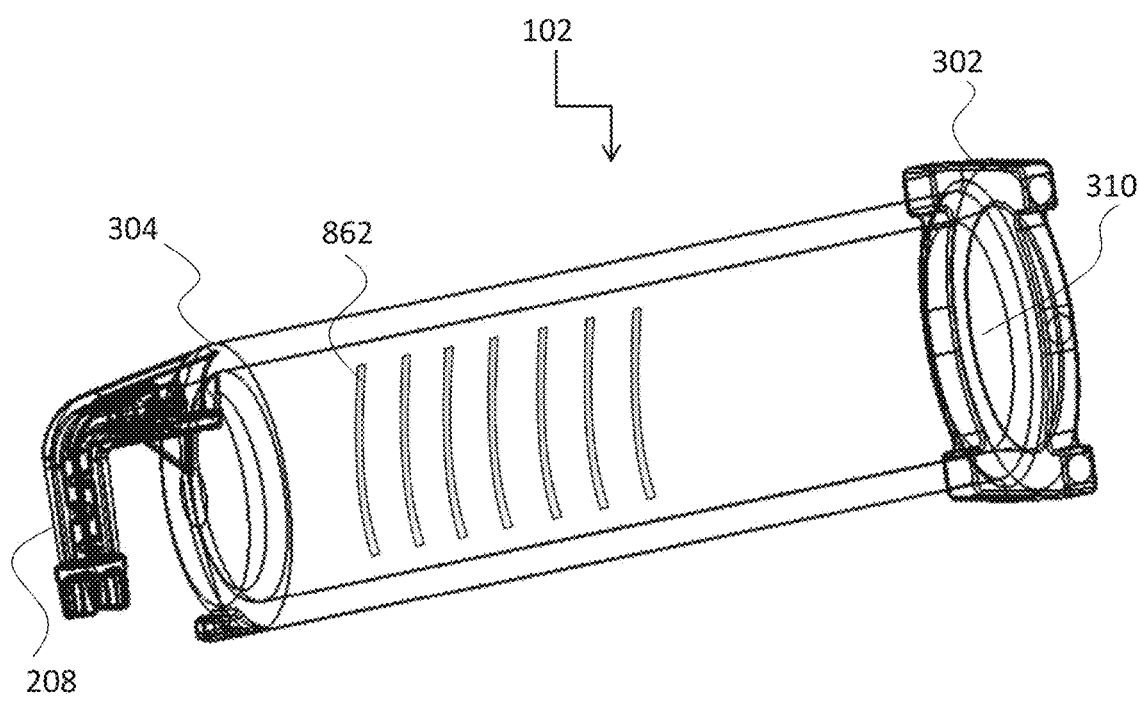
FIG. 8 schematically illustrates a perspective view of an exemplary cartridge having an optional light diffusing slot, in accordance with some embodiments of the current invention.

Reference is now made to FIG. 8, schematically illustrating a perspective view of an exemplary cartridge having at least one light diffusing slot, in accordance with some embodiments of the current invention.

In some embodiments, light diffusing section comprises at least one slot 862 in cartridge 102. In some embodiments, slots 862 are provided as etched elements in cartridge 102. Optionally, slots 862 are provided along an entire circumference of cartridge 102. Alternatively or additionally, slots 862 are provided along a portion of the circumference of cartridge 102. Alternatively or additionally, slots 862 are provided being parallel to a longitudinal axis of the cartridge 102. Optionally, longitudinally aligned slots 862 enhance the optical path of viewing the fluid inventory status of the medicament. Optionally the inner surface of a slot may be smooth and/or rough and/or having a varying roughness.

Exemplary Cartridge Having a Light Diffusing Plunger Contact

Figure 9:
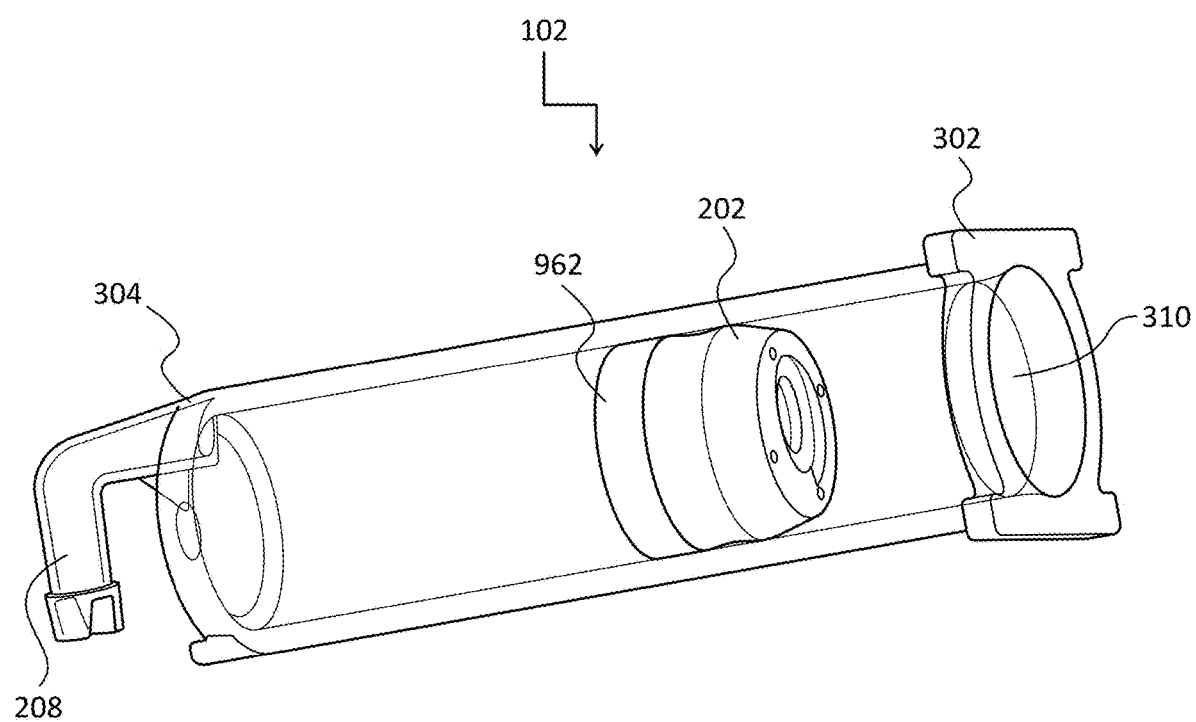
FIG. 9 schematically illustrates a perspective view of an exemplary cartridge having a plunger identifiable by a light diffusing surface, in accordance with some embodiments of the current invention.

Reference is now made to FIG. 9, schematically illustrating a perspective view of an exemplary cartridge having a plunger identifiable by diffusing and/or reflective light, in accordance with some embodiments of the current invention.

In some embodiments, plunger 202 defines a contact wall 962 with an inner wall of cartridge 102. In some embodiments, contact wall 962 serves as a light diffusing section by causing light to diffuse at the contact wall with plunger 202. In some embodiments, light emitted by contact wall 962 helps to identify the location of the plunger, potentially aiding in following a delivery of a medicament. In some embodiments, the light diffusing wall is at the proximal portion of the plunger (where the plunger contacts the medicament). Locating the light diffusing section at the proximal end of the plunger has the potential advantage of showing the contact point of the medicament with the plunger. Alternatively or additionally the light diffusing wall is at the distal end of the plunger. Alternatively or additionally, the light diffusing wall is located between the distal and proximal ends of the plunger. In some embodiments, indicia are provided for gauging the volume of medicament remained based on the location of the light diffusing wall of the plunger.

Exemplary Manufacturing Process

Figure 10:
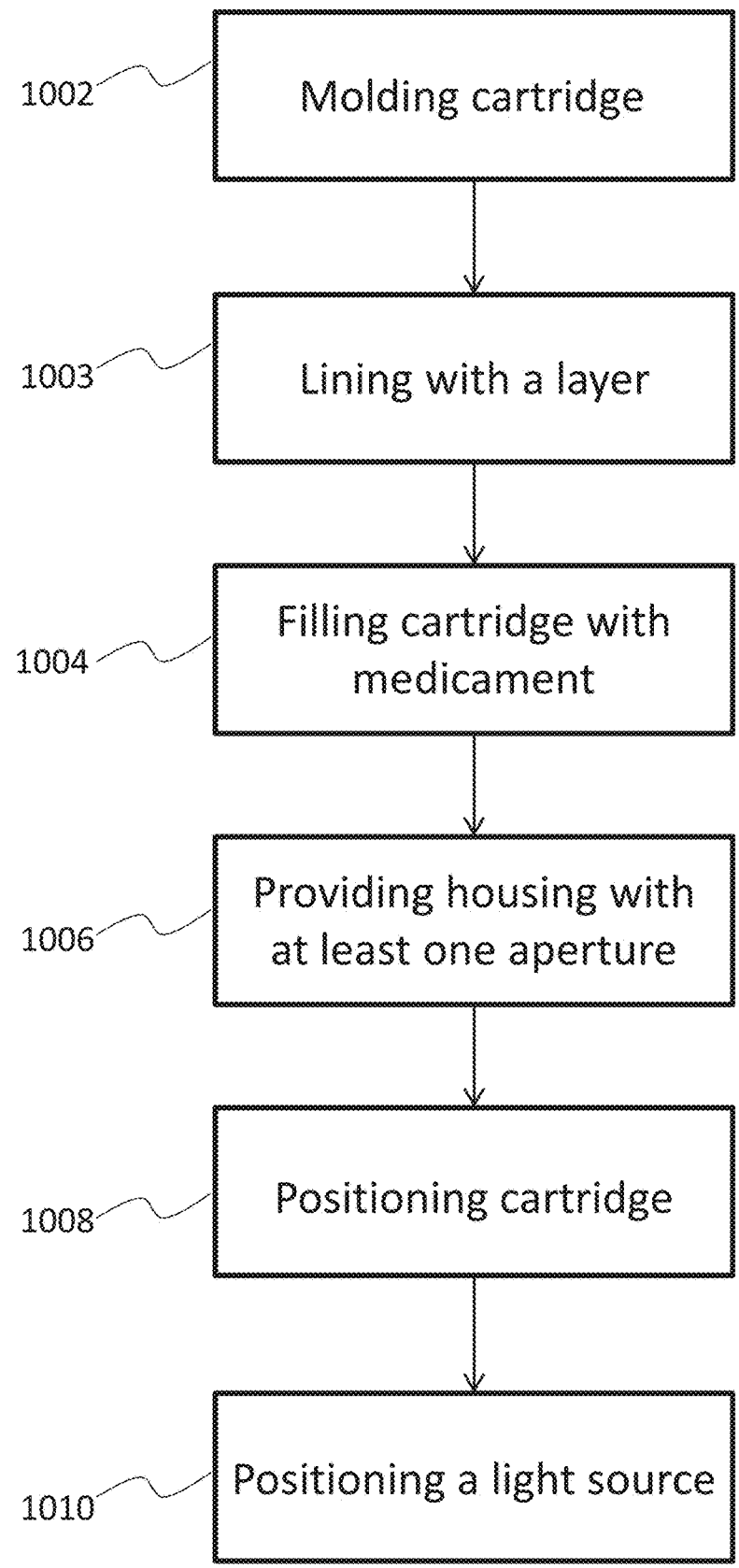
FIG. 10 is a flow chart illustrating an exemplary manufacturing process, in accordance with some embodiments of the current invention.

Reference is now made to FIG. 10 showing a flow chart illustrating an exemplary manufacturing process, in accordance with some embodiments of the current invention.

In some embodiments, a process begins by molding a cartridge 1002 configured for serving as a light pipe and having a light diffusing section. Optionally, the entire cartridge is molded using a transparent material, optionally a polymer, optionally, Crystal Zenith and/or glass. Alternatively or additionally, only a portion of a cartridge is molded using transparent material, optionally the portion defines a light input location. Optionally, the molded cartridge is coated internally with a second material layer, optionally having different light propagating characteristics than the molding material.

In some embodiments, after molding the cartridge, lining of the cartridge surface is provided 1003, for example, by lining at least a portion of the cartridge surface with a sticker, optionally a sticker which serves as a light diffuser, optionally lining the inner surface of the cartridge. Alternatively or additionally, the sticker lines the outside surface of the cartridge. In some embodiments, the sticker prevents at least a portion of the light from reaching the medicament, potentially useful when the medicament used is light-sensitive. In some embodiments, the sticker comprises a reflecting material. Alternatively or additionally, the sticker is provided with written text. Alternatively or additionally, the cartridge is provided with a layer of a light guiding element, optionally by linking in a chemical fashion.

In some embodiments, a sticker which is lined over at least a portion of the cartridge contains light-sensitive illustrations and/or text. Alternatively or additionally, the sticker contains fluorescent features which are detectable only when exposed to a specific range of wavelengths. For example, the sticker contains text and/or indicia which can only be seen when the embedded light source is on and/or when a specific wavelength is emitted. Optionally, the sticker is transparent, or semi-transparent, or opaque.

In some embodiments, once molded, a cartridge is filled with a medicament 1004. Optionally, the light input location and/or the transparent light pipe, and/or the light diffusing section are manufactured according to properties of the medicament being filled. For example, if the medicament is transparent, optionally having a non-transparent portion of the cartridge to avoid light traveling in uncontrolled set ups. Alternatively, when the medicament is light-sensitive, the cartridge is optionally coated with an opaque material.

In some embodiments, a housing having a window is provided 1006. In some embodiments, the cartridge is positioned in the housing 1008 such that the light diffusing section is aligned with the window. Optionally, the housing comprises a void sized and shaped to fit the cartridge. In some embodiments, the housing further comprises members sized and shaped to interlock with portions of the molded cartridge, such that a predefined orientation of the cartridge with respect to the housing is provided. In some embodiments, positioning of the cartridge is conducted such that at least a portion of the cartridge is viewed from the window. Optionally, the portion of the cartridge viewed from the window comprises the light diffusing section.

In some embodiments, at least one light source is positioned in the housing 1010. In some embodiments, the light source is positioned to have an optical path with at least a portion of the cartridge, optionally being a light input location.

Exemplary Manufacturing Light Indication Algorithm

Figure 11:
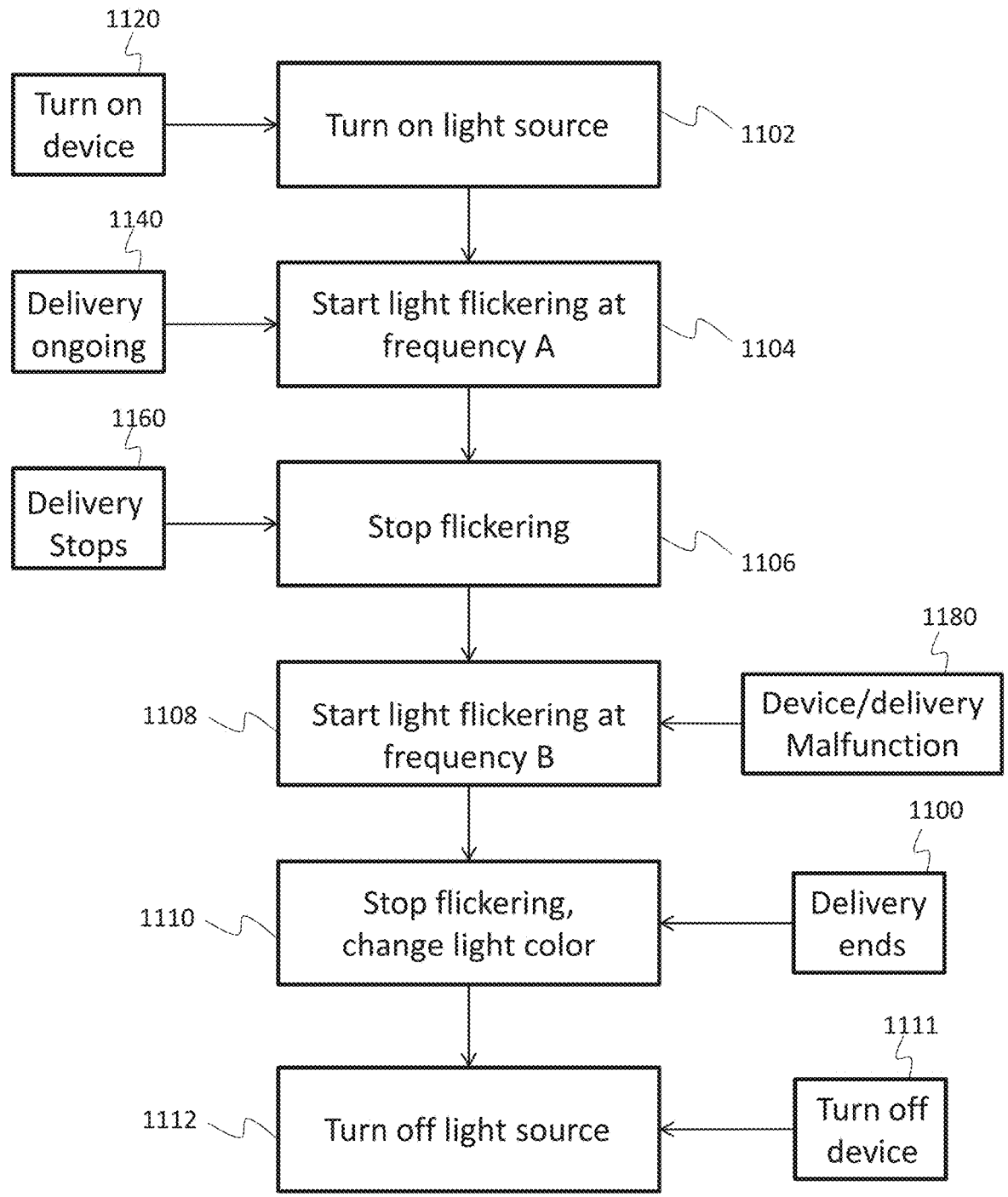
FIG. 11 is a flow chart illustrating an exemplary light indication algorithm, in accordance with some embodiments of the current invention.

Reference is now made to FIG. 11 showing a flow chart illustrating an exemplary light indication algorithm, in accordance with some embodiments of the current invention.

In some embodiments, light source is turned on 1102 once the device is turned on 1120, such as for example when electricity power is sensed by a control circuitry. Optionally, a user can start drug delivering. In some embodiments, while medicament delivery is ongoing 1140, the light flickers at flickering frequency A 1104. In some embodiments, when delivery stops 1160, the light source stops flickering 1106, optionally returning to the initial operating state. Alternatively the light source emits light having a different color.

In some embodiments, once a malfunction is identified 1180, the light flickers at frequency B 1108. In some embodiments, once delivery ends 1100, light flickering is stopped and optionally light changed color 1110. In some embodiments, when the device is turned off and/or removed from the user's body 1111, light is turned off 1112.

In some embodiments, improper use is also notified by light, such as when a user accidently removes a device while the device is delivering the medicament.

Optionally, a non-visual indication is also provided for any of the device state indications. For example, vibrations, optionally generated by the motor, are provided. Alternatively or additionally, sound indication may be provided for any indication of the device state.

Exemplary Method for Providing a User Indicator Light in a Drug Delivery Device

Figure 12:
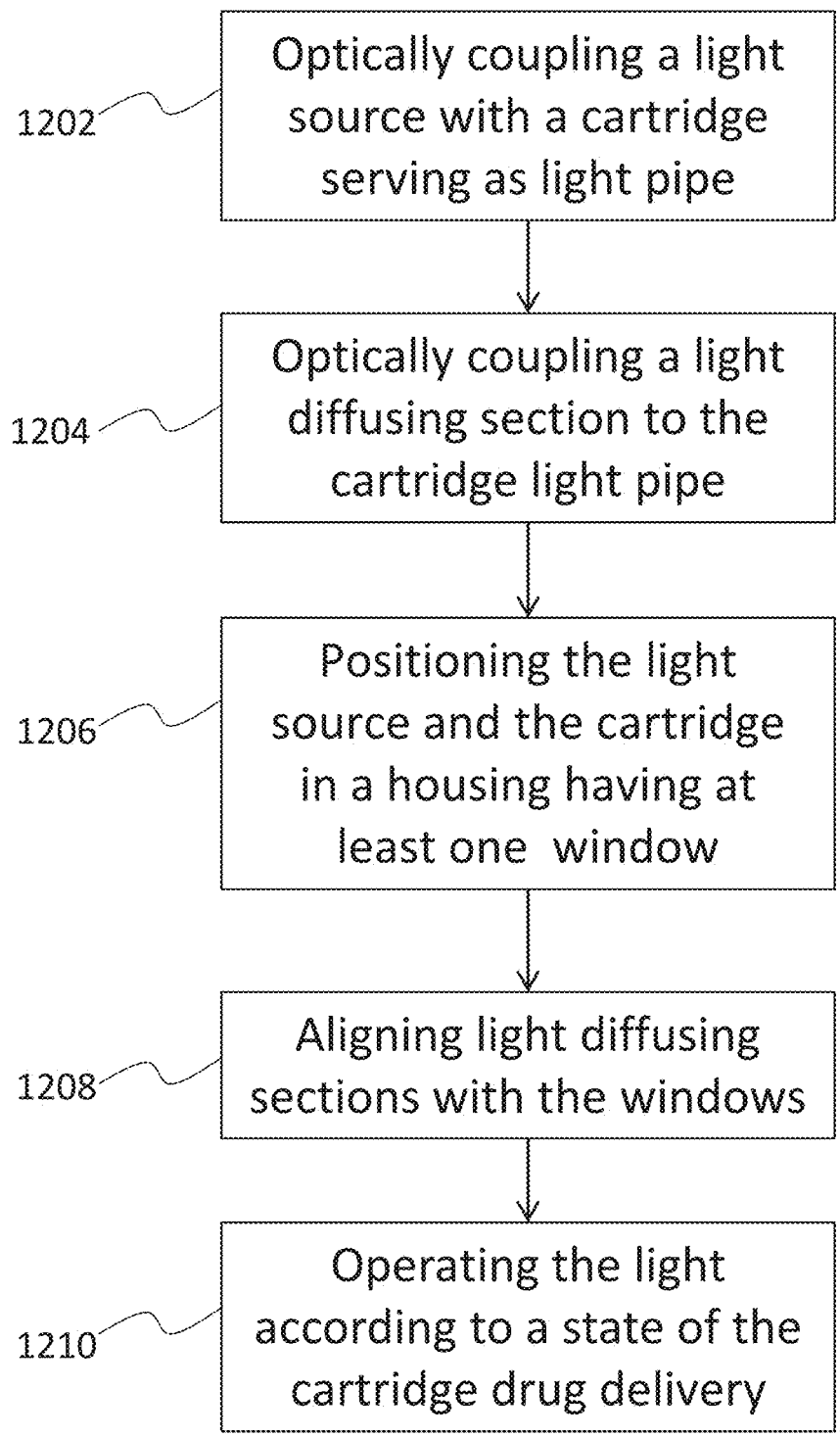
FIG. 12 is a flow chart illustrating an exemplary method for using a medicament cartridge as a user indicator light, in accordance with some embodiments of the current invention.

Reference is now made to FIG. 12 showing a flow chart illustrating an exemplary method for using a medicament cartridge as a user indicator light, in accordance with some embodiments of the current invention.

In some embodiments, a cartridge containing a medicament is used as a user indicator light by optically coupling a light source with a cartridge configured for serving as a light pipe for light generated by the light source 1202. In some embodiments, the cartridge further comprises at least one light diffusing section, which is optically coupled to the light pipe of the cartridge 1204, such that for example, light generated by the light source travels through the light pipe being the cartridge and diffuses out of the cartridge wall through the light diffusing element.

In some embodiments, the cartridge and the light source are positioned in a housing of a drug delivery device having a window 1206. Optionally, the cartridge and/or light source are aligned with respect to the window 1208, such that light generated by the light source travels through the light diffusing section and out of the window.

In some embodiments, the light is operated according to a state of the drug delivery device 1210, in accordance with device states as provided herein.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for indicating a state of a pharmaceutical delivery device to a user, the method comprising:
    optically coupling a light source to a cartridge, the cartridge comprising:
        a reservoir containing a fluid;
        a light pipe with a light input location; and
        a light diffusing section optically coupled to the light input location;
    positioning the light source and the cartridge in a housing of the pharmaceutical delivery device, the housing comprising a window;
    aligning the light diffusing section with the window of the housing to provide an optical pathway between at least part of the light diffusing section and an outside of the housing; and
    operating the light source to indicate a state of the pharmaceutical delivery device via diffusion of light from the light source through the light diffusing section and to the outside of the housing through the window.

2. The method of claim 1, wherein the state of the pharmaceutical delivery device comprises at least one of an ongoing delivery state, a stop delivery state, an on or off state, or a device malfunction state.

3. The method of claim 1, wherein the state of the pharmaceutical delivery device comprises an inventory status of the fluid.

4. The method of claim 1, wherein operating the light source comprises continuously or intermittently emitting light from the light source.

5. The method of claim 1, wherein operating the light source comprises changing a color of the light source.

6. A method of manufacturing a pharmaceutical delivery device, the method comprising:
    forming a cartridge, the cartridge comprising:
        a reservoir;
        a light pipe comprising an input location; and
        a light diffusing section optically coupled to the light pipe;
    filling the reservoir of the cartridge with a fluid;
    providing a housing defining a void and comprising a window that overlaps with the void;
    positioning the cartridge within the void of the housing such that the light diffusing section is aligned with the window of the housing to provide an optical pathway between at least part of the light diffusing section and an outside of the housing;
    positioning a light source within the housing; and
    optically coupling the light source to the light pipe through the input location such that when light from the light source enters the input location the light is diffused at the light diffusing section and exits to the outside of the housing through the window.

7. The method of claim 6, wherein forming the cartridge comprises molding the cartridge.

8. The method of claim 7, wherein molding the cartridge comprises molding the cartridge using a polymer.

9. The method of claim 6, further comprising operatively coupling the light source with control circuitry and programming to operate the light source according to a state of the pharmaceutical delivery device.

10. The method of claim 9, further comprising programming the control circuitry to adjust light generated by the light source according to an inventory status of the fluid.

11. The method of claim 6, wherein the light diffusing section is positioned to provide a view of a physical indicator of an inventory state of the fluid.

\* \* \* \* \*